(12) United States Patent
Yang et al.

(10) Patent No.: US 11,408,017 B2
(45) Date of Patent: Aug. 9, 2022

(54) COMPOSITION FOR PRODUCING TAGATOSE AND METHOD OF PRODUCING TAGATOSE USING THE SAME

(71) Applicant: CJ CheilJedang Corporation, Seoul (KR)

(72) Inventors: Sungjae Yang, Suwon-si (KR); Young Mi Lee, Suwon-si (KR); Il Hyang Park, Suwon-si (KR); Hyun Kug Cho, Suwon-si (KR); Seong Bo Kim, Seongnam-si (KR); Chan Hyoung Lee, Suwon-si (KR); Eun Jung Choi, Seongnam-si (KR); Sun Mi Shin, Seoul (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 0 days.

(21) Appl. No.: 16/582,629

(22) Filed: Sep. 25, 2019

(65) Prior Publication Data

US 2020/0087689 A1    Mar. 19, 2020

Related U.S. Application Data

(63) Continuation-in-part of application No. PCT/KR2018/003769, filed on Mar. 30, 2018.

(30) Foreign Application Priority Data

| Mar. 31, 2017 | (KR) | 10-2017-0042166 |
| Aug. 31, 2017 | (KR) | 10-2017-0111494 |
| Nov. 24, 2017 | (KR) | 10-2017-0158766 |

(51) Int. Cl.
*C12P 19/02* (2006.01)
*C12N 9/90* (2006.01)

(52) U.S. Cl.
CPC .................. *C12P 19/02* (2013.01)

(58) Field of Classification Search
None
See application file for complete search history.

(56) References Cited

U.S. PATENT DOCUMENTS

| 10,544,438 B2 * | 1/2020 | Kim | C12Y 501/03 |
| 2016/0186162 A1 * | 6/2016 | Oh | C12P 19/02 |
| | | | 435/148 |

FOREIGN PATENT DOCUMENTS

| CN | 101925609 B | 12/2013 | |
| CN | 105431541 A | 3/2016 | |
| CN | 106399427 A | 2/2017 | |
| KR | 10-744479 | 7/2007 | |
| KR | 10-0964091 | 6/2010 | |
| KR | 10-1057873 | 8/2011 | |
| KR | 10-1368731 | 2/2014 | |
| KR | 10-2014-0143109 A | 12/2014 | |
| KR | 10-1480422 | 1/2015 | |
| KR | 10-1550796 | 9/2015 | |
| WO | WO 2006/058092 A2 | 6/2006 | |
| WO | WO-2017059278 A1 * | 4/2017 | ..... C12Y 207/01144 |
| WO | WO-2019086054 A1 * | 5/2019 | .......... C12N 9/1205 |

OTHER PUBLICATIONS

Anderson et al., "D-Tagatose-6-phosphate Kinase from *Staphylococcus aureus*", Methods Enzymol. 90:87-91, 1982 (Year: 1982).*
Brenner, S., Trends Genet. 15:132-133, 1999 (Year: 1999).*
Scott et al., Nat. Genet. 21:440-443, 1999 (Year: 1999).*
UniProt Accession No. E8N0N6, Mar. 2016, 1 page (Year: 2016).*
Yamada et al., Int. J. Sys. Evol. Microbiol. 56:1331-1340, 2006 (Year: 2006).*
"Tagatose-6-phosphate kinase [Dictyoglomus thermophilum]", NCBI Reference Sequence: WP_012548536.1, 1 page, May 2013.
International Search Report and Written Opinion of the International Patent Application No. PCT/KR2018/003769, dated Jul. 23, 2018; 11 pages.
Wichelecki et al., "ATP-binding Cassette (ABC) Transport System Solute-binding Protein-guided Identification of NovelD-Altritol and Galactitol Catabolic Pathways in Agrobacterium tumefaciens C58", The Journal of Biological Chemistry, Nov. 27, 2015, vol. 290, No. 48, pp. 28963-28976.
Ito, Susumu "Catalysis, Structures, and Applications of Carbohydrate Epimerases", Journal of Applied Glycoscience, 2010, vol. 57, No. 1, pp. 1-6.
NCBI, GenBank accession No. WP_012582774.1, May 25, 2015; 1 page.
Tagatose 6-phosphate kinase, Dec. 11, 2013; retrieved on the Internet, retrieved on Sep. 29, 2020, URL: https://www.ncbi.nlm.nih.gov/protein/2173 35896; 1 page.
Tagatose 6-phosphate kinase, Jan. 18, 2017 retrieved on the Internet, retrieved on Sep. 29, 2020, URL: https://www.uniprot.org/uniprot/A9CES6.txt?version=51; 2 pages.
Putative tagatose-6-phosphate kinase, Jan. 18, 2017, retrieved on the Internet, retrieved on Sep. 28, 2020, URL: https://www.uniprot.org/uniprot/E8N0N6.txt?version=29; 1 page.
Tagatose-6-phosphate kinase, Jan. 18, 2017, retrieved on the Internet, retrieved on Sep. 28, 2020, URL: https://www.uniprot.org/uniprot/A0A0B3BKZ0.txt?version=15; 2 pages.
Database UniProt [Online], "Tagatose 6 phosphate kinase", Nov. 25, 2008, XP 55752483 A; 2 pages.
Database UniProt [Online], "Uncharacterized protein", Feb. 17, 2016, XP 55752670 A; 1 page.
Database UniProt [Online], "Putative tagatose-6-phosphate kinase", Apr. 5, 2011, XP 55752482 A; 1 page.

* cited by examiner

*Primary Examiner* — David Steadman
(74) *Attorney, Agent, or Firm* — Squire Patton Boggs (US) LLP

(57) ABSTRACT

Provided are a composition for producing tagatose, comprising fructose-4-epimerase, and a method of producing tagatose using the same.

5 Claims, 7 Drawing Sheets
Specification includes a Sequence Listing.

SEQUENCE LISTING

<160> NUMBER OF SEQ ID NOS: 14

<210> SEQ ID NO 1
<211> LENGTH: 425
<212> TYPE: PRT
<213> ORGANISM: Artificial Sequence
<220> FEATURE:
<223> OTHER INFORMATION: An amino acid sequence of Tagatose-6-phophate kinase, CJ_ANT_F4E derived from Anaerolinea thermophila

<400> SEQUENCE: 1

Met Thr Ala Ile Leu Glu Asn Leu Ala Ala Ala Arg Arg Ala Gly Lys
1               5                   10                  15

Pro Ala Gly Ile Thr Ser Val Cys Ser Ala His Pro Val Val Leu Arg
            20                  25                  30

Ala Ala Ile Arg Arg Ala Ala Ser Gln Thr Ala Val Leu Ile Glu
        35                  40                  45

Ala Thr Cys Asn Gln Val Asn His Leu Gly Gly Tyr Thr Gly Met Thr
    50                  55                  60

Pro Arg Asp Phe Val Ala Phe Val Asn Ser Ile Ala Ala Glu Glu Gly
65                  70                  75                  80

Leu Pro Ala Glu Leu Leu Ile Phe Gly Gly Asp His Leu Gly Pro Asn
                85                  90                  95

Pro Trp Arg Arg Glu Lys Ala Glu Asp Ala Leu Thr Lys Ala Ala Ala
            100                 105                 110

Met Val Asp Ala Tyr Val Thr Ala Gly Phe Arg Lys Ile His Leu Asp
        115                 120                 125

Ala Ser Met Gly Cys Ala Gly Glu Pro Ala Ala Leu Asp Asp Val Thr
    130                 135                 140

Ile Ala His Arg Ala Ala Lys Leu Thr Ala Val Ala Glu Lys Ala Ala
145                 150                 155                 160

Thr Glu Ala Gly Leu Pro Lys Pro Leu Tyr Ile Leu Gly Thr Glu Val
                165                 170                 175

Pro Val Pro Gly Gly Ala Asp His Val Leu Glu Thr Val Ala Pro Thr
            180                 185                 190

Glu Pro Gln Ala Ala Arg Asn Thr Ile Asp Leu His Arg Glu Ile Phe
        195                 200                 205

Ala Gln His Gly Leu Ser Asp Ala Phe Glu Arg Val Ile Ala Phe Val
    210                 215                 220

Val Gln Pro Gly Val Glu Phe Gly Ser Asp Asn Val Val Ala Tyr Asp
225                 230                 235                 240

Pro Gln Ala Ala Gln Ser Leu Ser Ala Val Leu Asp Gly Glu Pro Arg
                245                 250                 255

Leu Val Phe Glu Ala His Ser Thr Asp Tyr Gln Thr Glu Pro Ala Leu
            260                 265                 270

Ala Ala Leu Val Arg Asp Gly Tyr Pro Ile Leu Lys Val Gly Pro Gly
        275                 280                 285

Leu Thr Phe Ala Tyr Arg Glu Ala Leu Tyr Ala Leu Asp Met Ile Ala
    290                 295                 300

Ser Glu Met Val Gly Thr Tyr Gly Asp Arg Pro Leu Ala Arg Thr Met
305                 310                 315                 320

```
Glu Lys Leu Met Leu Ser Ala Pro Gly Asp Trp Gln Gly His Tyr His
            325                 330                 335

Gly Asp Asp Ile Thr Leu Arg Leu Gln Arg His Tyr Ser Tyr Ser Asp
            340                 345                 350

Arg Ile Arg Tyr Tyr Trp Thr Arg Pro Glu Ala Leu Ala Ala Val Ser
        355                 360                 365

Thr Leu His Lys Ala Leu Asp Gly Lys Thr Ile Pro Glu Thr Leu Leu
    370                 375                 380

Arg Gln Tyr Leu Gly Glu Leu Pro Leu Ala Ala Val Ala Gly Lys Glu
385                 390                 395                 400

Pro Glu Glu Val Leu Val Ala Ala Val Asp Gln Val Leu Ala Thr Tyr
            405                 410                 415

His Ala Ala Thr Gly Glu Gly Arg His
            420                 425

<210> SEQ ID NO 2
<211> LENGTH: 1278
<212> TYPE: DNA
<213> ORGANISM: Artificial Sequence
<220> FEATURE:
<223> OTHER INFORMATION: DNA sequence of Tagatose-6-phophate kinase,
      CJ_ANT_F4E derived from Anaerolinea thermophila

<400> SEQUENCE: 2
atgaccgcca ttttggaaaa tctcgccgcc gcgcgccgcg ccggcaaacc tgcgggcatc      60
acttcggtct gctcggccca ccccgttgtc ctgcgcgccg caatccgccg cgccgccgcc     120
agtcaaacgg ccgtactgat cgaggccacc tgcaatcagg tcaatcatct cggtggttat     180
accggcatga caccgcgtga cttcgttgcc ttcgtcaaca gcatcgccgc ggaagaagga     240
ctgcccgccg aactgctgat cttggcggc gatcatctcg gccccaatcc ctggcgcagg     300
gagaaggccg aggacgcgct gacaaaagcc gccgccatgg tcgacgccta tgtcacagct     360
ggttttcgca agatccacct tgatgcatcg atgggctgcg ccggtgagcc ggcagccctg     420
gatgacgtca ccatcgccca ccgcgccgcg aaactcacag ccgttgccga aaaggcagcc     480
actgaggctg gcctgccaaa accgctttat attctgggca ccgaagtgcc ggtgcccggc     540
ggtgccgacc atgtgcttga ccgtcgcaa ccgaccgaac cgcaggcggc gcgcaacacc     600
atcgatcttc atcgcgaaat cttttgcgcag cacggtcttt ccgatgcgtt cgaacgggtc     660
atcgcctttg tcgtgcagcc gggtgtggaa ttcggcagcg acaatgtcgt cgcttatgat     720
ccgcaggcag cgcagagcct gagcgccgtg ctggatgggc aaccgcgact ggtcttcgaa     780
gcccattcga ccgattacca gaccgagcct gcccttgcgg cactggtacg cgacggatat     840
ccgatcctca agttggacc gggcctcacc ttcgcttacc gggaagcgct ttatgcactc     900
gacatgatcg cctccgaaat ggtcggcacc tatggcgacc gaccgctggc gcggactatg     960
gaaaaattga tgttaagcgc gccgggcgac tggcagggcc attaccatgg cgacgacatc    1020
acgctccgat tgcaacgcca ttacagctac agcgaccgca tccgttacta ctggacgcga    1080
ccggaagcgc tcgcgccgt tccaccttg cataaggcac tggatgggaa gacaattccc    1140
gaaaccctgc tgcgccaata tctcggcgaa ttgccgctcg cggcggttgc gggaaaggaa    1200
ccggaggagg ttctggtcgc ggcggtggat caggtgctgg cgacctatca cgcggcgacg    1260
ggcgaaggcc gccactga                                                  1278

<210> SEQ ID NO 3
```

<211> LENGTH: 443
<212> TYPE: PRT
<213> ORGANISM: Artificial Sequence
<220> FEATURE:
<223> OTHER INFORMATION: Amino acids sequences of Tagatose-6-phophate kinase, CJ_AB_F4E derived from Anaerolineae bacterium

<400> SEQUENCE: 3

```
Met Thr Arg Asn Ser Pro Leu Ser Glu Val Ile Ala Ala Gln Lys Arg
1               5                   10                  15

Gly Glu Ser Arg Gly Ile Ala Ser Ile Cys Ser Ala Asn Pro Trp Val
            20                  25                  30

Ile Glu Ala Met Leu Gln Gln Ala Arg Ala Thr Gly Glu Pro Val Leu
        35                  40                  45

Ile Glu Ser Thr Cys Asn Gln Val Asn Gln Phe Gly Gly Tyr Thr Gly
    50                  55                  60

Trp Thr Pro Asp Gln Phe Met Ala Tyr Leu Arg Asp Leu Ala Pro Arg
65                  70                  75                  80

Gln Glu Phe Pro Phe Asp His Ile Ile Val Gly Gly Asp His Leu Gly
                85                  90                  95

Pro Ser Pro Trp Gln Asp Glu Pro Ala Ala Ile Ala Met Asp Lys Ala
            100                 105                 110

Lys Ile Leu Ile Arg Asp Cys Val Arg Ala Gly Tyr Thr Lys Ile His
        115                 120                 125

Leu Asp Ala Ser Met Lys Cys Ala Asp Asp Pro His Arg Pro Leu
    130                 135                 140

Asp Thr Arg Ile Ser Ala Ala Arg Ala Ala Glu Leu Ala Gln Val Ala
145                 150                 155                 160

Glu Lys Ala Phe Ser Glu His Pro Pro Gly Gly Ala Pro Pro Tyr Tyr
                165                 170                 175

Val Ile Gly Thr Glu Val Pro Leu Pro Gly Gly Val Gln Glu Gln Glu
            180                 185                 190

Glu Gly Leu Ser Val Thr Ser Ile Gly Asp Val Ala Gly Thr Ile Glu
        195                 200                 205

Ser Thr Lys Glu Ala Phe Phe Ala Arg Gly Leu Glu Arg Ala Trp Glu
    210                 215                 220

Arg Val Ile Ala Val Val Val Gln Pro Gly Val Glu Tyr Gly Asp Ala
225                 230                 235                 240

Thr Leu Phe Glu Tyr Asp Arg Ala Arg Ala Ala Asp Leu Ala Arg Phe
                245                 250                 255

Ile Glu Gly Tyr Asp Gly Leu Ile Tyr Glu Ala His Ser Thr Asp Tyr
            260                 265                 270

Gln Leu Ala Glu Ala Leu Arg Gln Leu Val Glu Asp His Phe Ala Ile
        275                 280                 285

Leu Lys Val Gly Pro Ala Leu Thr Phe Ser Phe Arg Glu Gly Val Phe
    290                 295                 300

Ala Leu Ala Ala Ile Glu Glu Leu Leu Ala Gly Arg Gln Asp Val
305                 310                 315                 320

Glu Pro Ser Arg Val Arg Glu Val Leu Asp Lys Thr Met Leu Ala Asn
                325                 330                 335

Pro Ile Tyr Trp Gln Lys Tyr Tyr Gln Gly Asp Gln Ala Val His
            340                 345                 350

Leu Lys Arg Lys Tyr Ser Phe Ser Asp Arg Ser Arg Tyr Tyr Trp Pro
        355                 360                 365

Val Pro Glu Val Gln Phe Ser Leu Ser Arg Leu Ile Gln Asn Leu Gly
```

```
                370             375             380
Glu Gln Pro Leu Pro Leu Thr Leu Leu Ser Gln Tyr Leu Pro Val Gln
385                 390                 395                 400

Tyr Ala Arg Ile Arg Gly Gly Glu Ile Ala Asn Val Pro Arg Ala Ile
                405                 410                 415

Leu Leu Asp Lys Val Arg Ser Val Leu Ser Asp Tyr Ser Tyr Ala Cys
                420                 425                 430

Gly Tyr Leu Thr Gly Pro Ala Arg Arg Asn Arg
            435                 440

<210> SEQ ID NO 4
<211> LENGTH: 1332
<212> TYPE: DNA
<213> ORGANISM: Artificial Sequence
<220> FEATURE:
<223> OTHER INFORMATION: DNA sequences of Tagatose-6-phophate kinase,
      CJ_AB_F4E derived from Anaerolineae bacterium

<400> SEQUENCE: 4
atgactcgga actcgcccct tatcagaggtg atcgctgccc agaaacgcgg cgagagcaga      60
gggatcgctt ccatatgctc ggccaatccc tgggtcatcg aggccatgct gcaacaggcc     120
cgcgcgaccg gcgaacctgt cctgatcgag tcgacctgca accaggtcaa tcaattcggc     180
ggctacaccg gttggacgcc ggatcaattc atggcctatc ttcgagattt ggcgccccgg     240
caagaatttc cctttgacca catcatcgtc ggcggcgatc atctcgggcc tagcccctgg     300
caagacgagc cggccgcgat agcgatggat aaggccaaga tcctgatccg ggattgcgtc     360
cgggcaggtt acaccaagat tcacctggac gccagcatga agtgcgccga cgacgatccc     420
catcggccgc tagataccag gatatctgcg gcccggggcgg ccgagctggc ccaggtggcc     480
gaaaaagcat tctccgagca cccaccaggc ggtgcgccgc cttattatgt gatcggcacc     540
gaggtgccct gcccggtgg ggttcaggaa caggaggagg gattgagtgt taccagtata     600
ggcgacgtgg ccggaaccat tgaatcgacc aaagaagcct tttttgcacg aggcttagaa     660
agggcttggg aacgggtcat agccgtcgtg gtgcaacccg cgtggagta tggtgatgcc     720
acgttatttg aatatgatcg ggctcgggcg ccgatctgg cccgatttat cgaaggttat     780
gatggcttga tatacgaagc gcattccact gattatcagt tagctgaggc actccggcag     840
ttggtagaag atcatttcgc catcttgaag gtggggccag cgctaacatt ttcatttcgg     900
gaggggggttt ttgccctggc tgccatagaa gaggagctgt tggccgggcg acaggatgtc     960
gaaccgtcac gggtgcgcga agttctggat aagaccatgt tggctaatcc aatctactgg    1020
cagaagtatt atcagggaga tgaccaggcc gtacatttga aaaggaaata tagttttagt    1080
gaccgttccc gatactattg gccggttccc gaggtgcaat tttctttgtc ccgactaatt    1140
caaaatttgg gagagcagcc gctgcctcta acgctcttaa gccaatacct gccggtccaa    1200
tacgcccgaa tcagaggtgg cgaaatagcc aatgttcccc gggcgatcct cttggataag    1260
gtcagaagcg tactctctga ttactcatat gcatgcggtt atctgaccgg ccctgctaga    1320
agaaaccgct ga                                                         1332

<210> SEQ ID NO 5
<211> LENGTH: 408
<212> TYPE: PRT
<213> ORGANISM: Artificial Sequence
<220> FEATURE:
<223> OTHER INFORMATION: An amino acid sequence of tagatose-6-phosphate
      kinase, CJ_DT_F4E derived from Dictyoglomus thermophilum
```

<400> SEQUENCE: 5

Met Trp Leu Ser Lys Asp Tyr Leu Arg Lys Gly Val Tyr Ser Ile
1               5                   10                  15

Cys Ser Ser Asn Pro Tyr Val Ile Glu Ala Ser Val Glu Phe Ala Lys
            20                  25                  30

Glu Lys Asn Asp Tyr Ile Leu Ile Glu Ala Thr Pro His Gln Ile Asn
        35                  40                  45

Gln Phe Gly Gly Tyr Ser Gly Met Thr Pro Glu Asp Phe Lys Asn Phe
    50                  55                  60

Val Met Gly Ile Ile Lys Glu Lys Gly Ile Glu Glu Asp Arg Val Ile
65                  70                  75                  80

Leu Gly Gly Asp His Leu Gly Pro Leu Pro Trp Gln Asp Glu Pro Ser
                85                  90                  95

Ser Ser Ala Met Lys Lys Ala Lys Asp Leu Ile Arg Ala Phe Val Glu
            100                 105                 110

Ser Gly Tyr Lys Lys Ile His Leu Asp Cys Ser Met Ser Leu Ser Asp
        115                 120                 125

Asp Pro Val Val Leu Ser Pro Glu Lys Ile Ala Glu Arg Glu Arg Glu
    130                 135                 140

Leu Leu Glu Val Ala Glu Glu Thr Ala Arg Lys Tyr Asn Phe Gln Pro
145                 150                 155                 160

Val Tyr Val Val Gly Thr Asp Val Pro Val Ala Gly Gly Gly Glu Glu
                165                 170                 175

Glu Gly Ile Thr Ser Val Glu Asp Phe Arg Val Ala Ile Ser Ser Leu
            180                 185                 190

Lys Lys Tyr Phe Glu Asp Val Pro Arg Ile Trp Asp Arg Ile Ile Gly
        195                 200                 205

Phe Val Ile Met Leu Gly Ile Gly Phe Asn Tyr Glu Lys Val Phe Glu
    210                 215                 220

Tyr Asp Arg Ile Lys Val Arg Lys Ile Leu Glu Glu Val Lys Lys Glu
225                 230                 235                 240

Asn Leu Phe Val Glu Gly His Ser Thr Asp Tyr Gln Thr Lys Arg Ala
                245                 250                 255

Leu Arg Asp Met Val Glu Asp Gly Val Arg Ile Leu Lys Val Gly Pro
            260                 265                 270

Ala Leu Thr Ala Ser Phe Arg Arg Gly Val Phe Leu Leu Ser Ser Ile
        275                 280                 285

Glu Asp Glu Leu Ile Ser Glu Asp Lys Arg Ser Asn Ile Lys Lys Val
    290                 295                 300

Val Leu Glu Thr Met Leu Lys Asp Asp Lys Tyr Trp Arg Lys Tyr Tyr
305                 310                 315                 320

Lys Asp Ser Glu Arg Leu Glu Leu Asp Ile Trp Tyr Asn Leu Leu Asp
                325                 330                 335

Arg Ile Arg Tyr Tyr Trp Glu Tyr Lys Glu Ile Lys Ile Ala Leu Asn
            340                 345                 350

Arg Leu Phe Glu Asn Phe Ser Glu Gly Val Asp Ile Arg Tyr Ile Tyr
        355                 360                 365

Gln Tyr Phe Tyr Asp Ser Tyr Phe Lys Val Arg Glu Gly Lys Ile Arg
    370                 375                 380

Asn Asp Pro Arg Glu Leu Ile Lys Asn Glu Ile Lys Lys Val Leu Glu
385                 390                 395                 400

Asp Tyr His Tyr Ala Val Asn Leu

<210> SEQ ID NO 6
<211> LENGTH: 1227
<212> TYPE: DNA
<213> ORGANISM: Artificial Sequence
<220> FEATURE:
<223> OTHER INFORMATION: DNA sequence of tagatose-6-phosphate kinase, CJ_DT_F4E derived from Dictyoglomus thermophilum

<400> SEQUENCE: 6

```
atgtggctta gtaaagatta tttgagaaaa aagggagttt attctatatg tagctctaat      60
ccatatgtga ttgaggcaag tgttgaattt gctaaggaga agaatgatta tattttaatt     120
gaggcgacac ctcatcagat aaaccagttt ggtggatatt caggtatgac tcccgaagat     180
tttaaaaact tgtaatggg aataataaaa gaaaagggaa tagaagagga tagggtgatt      240
cttggagggg accatttagg ccctctccct tggcaagatg aaccttcttc ttctgcaatg     300
aaaaaggcaa agaccttat aagggccttt gtggagagtg ttataagaa gatacacctt       360
gattgtagta tgtctctttc tgatgatcct gtagtgctct ctcccgagaa gatagcagaa     420
agggagaggg aacttcttga ggttgcagaa gagactgcta gaaagtacaa ttttcagcct     480
gtgtatgtgg tgggaactga tgtaccggta gctggaggag gcgaagagga aggtattacc     540
tcagtggagg attttagagt agcaatctcc tctttaaaaa aatattttga ggatgttcca     600
aggatatggg ataggataat tggttttgta ataatgcttg gtataggttt taattatgaa     660
aaagtgtttg agtatgacag gattaaggtg agaaaaattt tagaggaggt aaagaaagag     720
aatctttttg ttgaaggtca ctctactgac tatcagacaa aacgtgcatt gagagatatg     780
gtagaggatg gagtaagaat tcttaaggtt ggtcctgctt taacagcaag ttttagaagg     840
ggagtatttt tattaagtag cattgaggat gagcttatat cggaagataa aaggtctaat     900
attaagaaag ttgtgcttga gactatgtta aaagatgata aatattggag aaagtattat     960
aaggattcag aaagattaga attagatatt tggtacaact tacttgatag gattagatat    1020
tattgggaat ataaagagat aaaaatagct ttaaataggc ttttttgaaaa ttttttcggaa   1080
ggggttgata ttagatacat ctatcaatat ttttatgatt cgtatttttaa agtaagagaa   1140
ggaaaaataa gaaatgatcc aagggagcta ataaagaatg aaataaagaa ggtcttggag    1200
gactatcact atgctgtaaa cttataa                                       1227
```

<210> SEQ ID NO 7
<211> LENGTH: 429
<212> TYPE: PRT
<213> ORGANISM: Artificial Sequence
<220> FEATURE:
<223> OTHER INFORMATION: An amino acid sequence of tagatose-6-phosphate kinase, CJ_ANTA_F4E derived from Anaerolinea thermophila

<400> SEQUENCE: 7

Met Met Phe Gly Ser Pro Ala Pro Leu Leu Asp Met Val Thr Ala Gln
1               5                   10                  15

Lys Gln Gly Met Ala Arg Gly Ile Pro Ser Ile Cys Ser Ala His Pro
            20                  25                  30

Val Val Leu Ser Ala Ala Cys His Leu Ala Arg Arg Ser Gly Ala Pro
        35                  40                  45

Leu Leu Ile Glu Thr Thr Cys Asn Gln Val Asn His Gln Gly Gly Tyr
    50                  55                  60

Ser Gly Met Thr Pro Ala Asp Phe Val Arg Phe Leu Arg Glu Ile Leu

```
            65                  70                  75                  80
Glu Arg Glu Gly Ile Pro Pro Gln Gln Val Ile Leu Gly Gly Asp His
                85                  90                  95

Leu Gly Pro Tyr Pro Trp Arg Lys Glu Pro Ala Glu Thr Ala Ile Ala
            100                 105                 110

Gln Ala Leu Glu Met Val Arg Ala Tyr Val Gln Ala Gly Tyr Thr Lys
            115                 120                 125

Ile His Leu Asp Ala Ser Met Pro Cys Ala Asp Asp Pro Glu Arg
    130                 135                 140

Pro Leu Pro Leu Glu Arg Ile Ala Arg Arg Ala Ala Gln Leu Cys Ala
145                 150                 155                 160

Ala Ala Glu Ala Ala Ala Gly Ala Val Gln Pro Val Tyr Val Ile Gly
                165                 170                 175

Ser Glu Val Pro Pro Gly Gly Ala Gln Gly Gln Glu Ala Arg Leu
    180                 185                 190

His Val Thr Thr Pro Gln Glu Ala Gln Ala Ala Leu Asp Ala Phe Arg
            195                 200                 205

Glu Ala Phe Leu Gln Ala Gly Leu Thr Pro Val Trp Glu Arg Val Ile
    210                 215                 220

Ala Leu Val Val Gln Pro Gly Val Glu Phe Gly Val Asp Ser Ile His
225                 230                 235                 240

Ala Tyr Gln Arg Glu Ala Ala Arg Pro Leu Lys Thr Phe Ile Glu Gly
                245                 250                 255

Val Pro Gly Met Val Tyr Glu Ala His Ser Thr Asp Tyr Gln Thr Arg
            260                 265                 270

Ala Ser Leu Arg Ala Leu Val Glu Asp His Phe Ser Ile Leu Lys Val
        275                 280                 285

Gly Pro Ala Leu Thr Phe Ala Tyr Arg Glu Ala Val Phe Ala Leu Glu
    290                 295                 300

His Ile Glu Arg Glu Ile Leu Gly Arg Gln Asp Met Pro Leu Ser Arg
305                 310                 315                 320

Leu Ser Glu Val Leu Asp Glu Val Met Leu Asn Asp Pro Arg His Trp
                325                 330                 335

Gln Gly Tyr Phe Ala Gly Ala Pro Ala Glu Gln Ala Leu Ala Arg Arg
            340                 345                 350

Tyr Ser Phe Ser Asp Arg Ile Arg Tyr Tyr Trp His His Pro Ala Ala
        355                 360                 365

Gln Glu Ala Val Arg Arg Leu Leu Ala Asn Leu Ile Glu Thr Pro Pro
    370                 375                 380

Pro Leu Ser Leu Leu Ser Gln Tyr Leu Pro Arg Glu Tyr Glu Met Val
385                 390                 395                 400

Arg Ala Gly Glu Ile Ser Ser His Pro Gln Asp Leu Ile Arg Ala His
                405                 410                 415

Ile Gln His Thr Leu Glu Asp Tyr Ala Ala Ala Cys Gly
            420                 425

<210> SEQ ID NO 8
<211> LENGTH: 1290
<212> TYPE: DNA
<213> ORGANISM: Artificial Sequence
<220> FEATURE:
<223> OTHER INFORMATION: DNA sequence of tagatose-6-phosphate kinase,
      CJ_ANTA_F4E derived from Anaerolinea thermophila

<400> SEQUENCE: 8
```

```
atgatgttcg gctcgcctgc tcccctgctg gatatggtca ccgcgcagaa acagggcatg      60
gcgcggggta tcccatccat ttgttcggca catccggtgg tgctgagtgc cgcctgccat     120
cttgcccgcc ggagcggcgc gcccctgctc atcgaaacca cctgcaatca ggtcaaccac     180
caaggtgggt acagcggcat gaccccgcc gattttgtcc gctttctgcg cgaaattctg      240
gaacgggaag gtattccccc gcaacaggtc atcctgggcg gggatcacct gggtccttac     300
ccctggcgga agagcctgcc gaaaccgcc atagcacaag cgctggaaat ggtgcgggca      360
tacgtgcagg caggctacac caaaattcat ctggacgctt ccatgccctg cgccgatgac     420
gaccccgagc gtcccctgcc gctggagcgc atagcccgac gggcggcgca gttgtgcgcc     480
gccgccgaag ccgccgcggg agcggttcag ccggtgtacg taattggcag tgaggtgccc     540
ccgcccggcg gcgcgcaggg tcaggaggca agacttcacg tcaccactcc gcaggaagcc     600
caagccgcgc tggatgcctt cgggaagcc tttctgcagg caggcttgac tcccgtttgg      660
gagcgggtca ttgcgctggt agtccagccg ggggtggagt ttggcgtgga cagcattcac     720
gcctatcagc gcgaagccgc ccgcccgctg aagaccttca tcgagggcgt gcccggcatg     780
gtgtatgaag cccactcgac cgattaccag acccgtgcct ccctgcgtgc gctggtggaa     840
gaccactttt ccattctcaa ggttggtccg gcactaacct ttgcctaccg cgaagccgtg     900
ttcgccctgg aacacatcga acgggaaata ttgggcaggc aggatatgcc tctctcccgc     960
ctgagtgaag tcctcgacga ggtgatgctg aacgatccac gccactggca gggatacttt    1020
gccggcgctc ccgccgaaca ggcgctggcg cgccgctaca gtttcagcga ccgcattcgc    1080
tattactggc accatcccgc cgcgcaggaa gccgtgcgga gactgctcgc caacctgatc    1140
gaaaccccgc cgccgctgag tttgctcagc cagtacctgc cgcgcgagta tgagatggtg    1200
cgcgcggggg aaatctccag ccacccgcag gacctgattc gggcacatat ccagcacacg    1260
ctggaagatt acgctgcggc gtgcgggtaa                                     1290
```

<210> SEQ ID NO 9
<211> LENGTH: 394
<212> TYPE: PRT
<213> ORGANISM: Artificial Sequence
<220> FEATURE:
<223> OTHER INFORMATION: An amino acid sequence of tagatose-6-phosphate kinase, CJ_TH_F4E derived from Thermobifida halotolerans

<400> SEQUENCE: 9

Met Ser Val Ile Pro Lys Glu Thr Gly Val Ser Pro Ser Arg Leu Asn
1               5                   10                  15

Val Pro Ser Arg Leu Gly Val Gly Pro Met Ser Lys Asn Ala Val Asp
            20                  25                  30

Ala Ala Ile Ser Val Ala Ala Arg Ala Asp Gln Pro Leu Met Leu Ile
        35                  40                  45

Pro Ser Arg Arg Gln Val Glu Ala Ala Ser Gln Gly Gly Gly Tyr Val
    50                  55                  60

Glu Gln Trp Asp Thr Ala Ala Phe Ala Asp Tyr Val Arg Arg Asn Asp
65                  70                  75                  80

Leu Val Gly Arg Ile Leu Leu Cys Arg Asp His Gly Gly Pro Tyr Gln
                85                  90                  95

Ser Pro Arg Glu Arg Glu Gln Arg Leu Pro Leu Asp Ala Ala Met Ala
            100                 105                 110

Ser Ala Leu Glu Ser Tyr Lys Glu Asp Ile Arg Cys Gly Phe Asp Leu
        115                 120                 125

```
Leu His Ile Asp Thr Ser Met Asp Leu Asp Gly Val Ala Asp Glu Ser
130                 135                 140
Ala Ala Ile Asp Arg Ala Leu Glu Leu Tyr Gly Gln Cys Val Glu Phe
145                 150                 155                 160
Ala Arg Ser Gln Gly Arg Glu Val Met Phe Glu Ile Gly Phe Glu Asp
            165                 170                 175
Gln Gly Arg Asp Thr Asn Asp Pro Phe Glu Phe Gln Glu Leu Leu Asp
            180                 185                 190
Glu Ala Leu Glu Gly Leu Arg Lys Ala Asp Leu Pro Ala Pro Thr Phe
            195                 200                 205
Val Val Ala Gln Thr Gly Thr Lys Val Val Glu Thr Gly Asn Thr Gly
210                 215                 220
Gly Ile Gly Val Ala Pro Ser Ala Val Gly Val Ala Val Arg Ala Leu
225                 230                 235                 240
Ala Asp Val Val Glu Arg Asn Gly Ile Ala Leu Lys Ala His Asn Cys
                245                 250                 255
Asp Tyr Leu Asp Glu Ser Thr Val Gly Tyr Leu Ala Ala Ser Gly Val
            260                 265                 270
His Ala Leu Asn Val Ala Pro Glu Phe Gly Val Glu Thr Arg Ala
            275                 280                 285
Phe Ile Gly Val Leu Gln Glu Leu Gly Leu Gly Val Gln Arg Glu Arg
290                 295                 300
Phe Leu Ala Leu Ala Tyr Glu Ser Gly Ser Trp Lys Lys Trp Met Ala
305                 310                 315                 320
Gln Asn Thr Thr Ala Thr Asp Tyr Asp Arg Ala Val Ile Ala Gly His
                325                 330                 335
Tyr Val Tyr Gly Thr Asp Glu Phe Lys Glu Ile Lys Thr Ala Ala Gln
            340                 345                 350
Gln Ile Ala Gln Ser Arg Gly Ile Asp Val Asp Thr Arg Leu Arg Glu
            355                 360                 365
Ala Val Ala Ala Ser Ile Glu Asn Tyr Ala Arg Pro Leu Arg Glu Val
            370                 375                 380
Ala Ala Ala Ala Ser Ala Pro Ala Ala Ala
385                 390
```

<210> SEQ ID NO 10
<211> LENGTH: 1185
<212> TYPE: DNA
<213> ORGANISM: Artificial Sequence
<220> FEATURE:
<223> OTHER INFORMATION: DNA sequence of tagatose-6-phosphate kinase, CJ_TH_F4E derived from Thermobifida halotolerans

<400> SEQUENCE: 10

```
atgtccgtta tcccgaaaga gaccggtgtt tccccgagcc gactgaatgt tccctcacgg     60
ctgggggtgg gaccgatgtc gaagaacgcg gtggacgcgg cgatcagcgt ggcggcccgc    120
gccgaccagc cgctgatgct catccccagc cggcgccagg tcgaggcggc gtctcagggc    180
ggcggctacg tcgagcagtg ggacaccgcg gcgttcgccg actacgtgcg ccgcaacgac    240
cttgtgggac ggatcctgct gtgcagggac cacgaggcc cctaccagtc cccgcgggag    300
cgggagcagc ggctcccccct cgacgcggcg atggcctccg cgctggagtc ctacaaggag    360
gacatccgct gcggtttcga cctgctgcac atcgacacct ccatggacct cgacggagtc    420
gccgacgagt cggcggcgat cgaccgggcg ctggagctct acgggcagtg cgtcgagttc    480
gcccgttccc aggggcggga ggtgatgttc gagatcggct cgaggaccca gggaagggac    540
```

```
accaacgacc cgttcgagtt ccaggagctc ctcgacgagg cgctggaggg gctgcgcaag      600
gcggacctgc ccgccccgac cttcgtcgtc gcgcagacgg ggaccaaggt cgtcgagacc      660
ggcaacaccg gcgggatcgg ggtcgcgccc agcgcggtcg tgtcgccgt gcgcgcgctg       720
gccgacgtcg tggagcggaa cggcatcgcc ctcaaggcgc acaactgcga ctacctggac      780
gagagcacgg tcgggtacct ggccgcctcc ggtgtgcacg cgctgaacgt cgctccggag      840
ttcggcgtgg tcgagacgcg ggcgttcatc ggcgtactgc aggagctggg cctgggcgtg      900
cagcgggagc gcttcctcgc cctggcctac gagtccggct cgtggaagaa gtggatggcc      960
cagaacacca cggccaccga ctacgaccgc gccgtgatcg ccggccacta cgtctacggc     1020
acggacgagt tcaaggagat caagaccgcg gcccagcaga tcgcgcagtc ccggggcatc     1080
gacgtcgaca cccggctgcg tgaggccgtc gccgcgtcga tcgagaacta cgcgcgaccg     1140
ctgcgcgaag tcgccgcggc ggcttccgcc cccgcggcgg cgtga                    1185
```

<210> SEQ ID NO 11
<211> LENGTH: 446
<212> TYPE: PRT
<213> ORGANISM: Artificial Sequence
<220> FEATURE:
<223> OTHER INFORMATION: An amino acid sequence of tagatose-6-phosphate
      kinase, CJ_TAI_F4E derived from Thermoanaerobacter indiensis

<400> SEQUENCE: 11

```
Met Asn Thr Glu His Pro Leu Lys Asn Val Val Lys Leu Gln Lys Lys
1               5                   10                  15

Gly Ile Pro Ile Gly Ile Tyr Ser Val Cys Ser Ala Asn Glu Ile Val
            20                  25                  30

Ile Gln Val Ala Met Glu Lys Ala Leu Ser Met Asp Ser Tyr Val Leu
        35                  40                  45

Ile Glu Ala Thr Ala Asn Gln Val Asn Gln Tyr Gly Gly Tyr Thr Asn
    50                  55                  60

Met Lys Pro Ile Asp Phe Arg Asp Phe Val Tyr Ser Ile Ala Lys Arg
65                  70                  75                  80

Ile Asn Phe Pro Glu Asn Arg Ile Ile Leu Gly Gly Asp His Leu Gly
                85                  90                  95

Pro Leu Pro Trp Lys Asn Gln Gln Ala Lys Lys Ala Met Glu Glu Ala
            100                 105                 110

Lys Glu Leu Val Lys Gln Phe Val Met Ala Gly Phe Thr Lys Ile His
        115                 120                 125

Val Asp Thr Ser Met Phe Leu Gly Asp Asp Asn Ile Asn Ile Lys Leu
    130                 135                 140

Asp Thr Glu Thr Ile Ala Glu Arg Gly Ala Ile Leu Val Ser Val Ala
145                 150                 155                 160

Glu Arg Ala Phe Glu Glu Leu Lys Lys Ser Asn Pro Tyr Ala Leu His
                165                 170                 175

Pro Val Tyr Val Ile Gly Ser Glu Val Pro Val Pro Gly Gly Ser Gln
            180                 185                 190

Lys Glu Asn Asn Asn Glu Ile Gln Val Thr Lys Pro Ala Asp Phe Glu
        195                 200                 205

Glu Thr Val Glu Val Tyr Lys Ser Thr Phe Tyr Lys Tyr Gly Leu Gly
    210                 215                 220

Asn Ala Trp Glu Asp Val Val Ala Val Val Gln Pro Gly Val Glu
225                 230                 235                 240
```

```
Phe Gly Val Glu Asn Ile His Glu Tyr Asp His Gln Gln Ala Glu Asn
                245                 250                 255

Leu Val Ser Ala Leu Lys Lys Tyr Pro Asn Leu Val Phe Glu Ala His
            260                 265                 270

Ser Thr Asp Tyr Gln Pro Ala Lys Leu Leu Lys Glu Met Val Arg Asp
        275                 280                 285

Gly Phe Ala Ile Leu Lys Val Gly Pro Glu Leu Thr Phe Ala Leu Arg
    290                 295                 300

Glu Gly Leu Phe Ala Leu Asn Ile Ile Glu Lys Glu Leu Phe Lys Asp
305                 310                 315                 320

Asn His Asp Ile Glu Met Ser Asn Phe Ile Asp Ile Leu Asp Thr Ala
                325                 330                 335

Met Leu Asn Asn Pro Lys Tyr Trp Glu Gln Tyr Tyr Tyr Gly Asp Asp
            340                 345                 350

Asn Lys Ile Arg Ile Ala Arg Lys Tyr Ser Tyr Ser Asp Arg Cys Arg
        355                 360                 365

Tyr Tyr Leu Ile Glu Asn Glu Val Arg Ala Ser Met Ser Arg Leu Phe
    370                 375                 380

Lys Asn Leu Thr Asn Val Glu Ile Pro Leu Thr Leu Ile Ser Gln Tyr
385                 390                 395                 400

Met Pro Ile Gln Tyr Glu Lys Ile Arg Met Gly Leu Leu Lys Asn Asp
                405                 410                 415

Pro Glu Asn Leu Val Lys Asp Lys Ile Gly Asn Cys Ile Asp Lys Tyr
            420                 425                 430

Leu Tyr Ala Thr Asn Pro Thr Ser Gly Glu Phe Lys Leu Ile
        435                 440                 445

<210> SEQ ID NO 12
<211> LENGTH: 1341
<212> TYPE: DNA
<213> ORGANISM: Artificial Sequence
<220> FEATURE:
<223> OTHER INFORMATION: DNA sequence of tagatose-6-phosphate kinase,
      CJ_TAI_F4E derived from Thermoanaerobacter indiensis

<400> SEQUENCE: 12
atgaatacag aacatccttt gaaaaacgtt gttaaactac aaaaaaaggg aattccaata      60
ggtatttatt cagtttgtag tgcaaatgaa atagttattc aagttgcaat ggagaaggca     120
ttgagtatgg atagttatgt tttaattgaa gcaacggcta atcaagtaaa tcaatatggt     180
ggctatacga atatgaaacc tattgatttt agagattttg tgtattctat agccaaaagg     240
ataaacttcc agaaaatag aataatcctt ggcggggacc acttaggacc tttgccatgg     300
aaaaatcaac aagcgaaaaa agcaatggaa gaagcaaaag aacttgttaa caatttgtg     360 atggctggct ttacgaaaat tcatgtagat acaagtatgt tcttggaga tgataacata     420 aatatcaaac tagatactga actattgcg gagagaggag cgatacttgt atcagtagca     480
gaaagagctt ttgaggagtt aaaaaagtct aatccttatg ctcttcatcc agtttatgta     540
ataggtagtg aagttcctgt tccaggaggt tctcaaaaag aaaataataa tgaaatacaa     600
gtaacaaagc cggcggattt tgaagaaact gtggaagtgt ataaaagcac tttctataaa     660
tatggtttag gaaacgcatg ggaagatgtt gtagcagtgg ttgtgcagcc tggggtggaa     720
tttggagttg aaaatattca tgaatatgat caccaacagg ctgaaaattt agtaagtgct     780
ttaaaaaagt atcctaattt agtattgaa gcccactcta cggattatca acctgcaaaa     840
ctactaaaag aaatggtgag agatggattt gctatactta agttggacc tgaattgact     900
```

```
tttgcattaa gggaaggatt gtttgctctg aatattatag aaaaagaatt atttaaagat       960
aatcatgata ttgagatgtc aaattttatt gatatccttg atacagcaat gttaaataat      1020
ccgaagtatt gggaacagta ttattacggt gatgataata aaattagaat tgctagaaaa      1080
tacagctatt ctgatagatg taggtattat ctaatcgaaa atgaagttag agcatctatg      1140
tctaggttgt ttaaaaattt aacaaatgtt gagataccat taaccttaat aagtcagtat      1200
atgcctattc aatatgaaaa aattagaatg ggactattaa aaaatgatcc tgagaattta      1260
gtaaaagata aaattggaaa ttgcattgat aagtatttgt atgctactaa tccgacaagt      1320
ggagaattta aactaatata a                                                1341

<210> SEQ ID NO 13
<211> LENGTH: 38
<212> TYPE: DNA
<213> ORGANISM: Artificial Sequence
<220> FEATURE:
<223> OTHER INFORMATION: primer DNA sequence of CJ_ANT_F4E or
      CJ_ANTA_F4E

<400> SEQUENCE: 13
atatacatat gatgttcggc tcgcctgctc ccctgctg                                38

<210> SEQ ID NO 14
<211> LENGTH: 38
<212> TYPE: DNA
<213> ORGANISM: Artificial Sequence
<220> FEATURE:
<223> OTHER INFORMATION: primer DNA sequence of CJ_ANT_F4E or
      CJ_ANTA_F4E

<400> SEQUENCE: 14
tggtgctcga gcccgcacgc cgcagcgtaa tcttccag                                38
```

COMPOSITION FOR PRODUCING TAGATOSE AND METHOD OF PRODUCING TAGATOSE USING THE SAME

CROSS REFERENCE TO RELATED APPLICATIONS

The present application is a continuation-in-part of International Application No. PCT/KR2018/003769, filed Mar. 30, 2018, which claims the benefit of Korean application nos. 10-2017-0158766, filed Nov. 24, 2017, 10-2017-0111494, filed Aug. 31, 2017, and 10-2017-0042166, filed Mar. 31, 2017, the contents of which are hereby incorporated by reference in their entireties.

INCORPORATION BY REFERENCE OF SEQUENCE LISTING

This application includes an electronically submitted sequence listing in .txt format. The .txt file contains a sequence listing entitled "059520.00013_ST25.txt" created on Dec. 2, 2019 and being 35,231 bytes in size. The sequence listing contained in this .txt file is part of the specification and is hereby incorporated by reference herein in its entirety.

BACKGROUND OF THE INVENTION

1. Field of the Invention

The present disclosure relates to a composition for producing tagatose, comprising fructose-4-epimerase, and a method of producing tagatose using the same.

2. Description of the Related Art

Tagatose is a natural sweetener, which is present in a small amount in foods such as milk, cheese, cacao, etc., and in sweet fruits such as apples and mandarin, and has a physical property similar to sucrose. Tagatose has a calorie value of 1.5 kcal/g which is one third that of sucrose, and a glycemic index (GI) of 3 which is 5% that of sucrose. Tagatose has a sweet taste similar to sucrose and various health benefits. In this regard, tagatose can be used as an alternative sweetener capable of satisfying both taste and health when applied to a wide variety of products.

Conventionally known methods of producing tagatose include a chemical method (a catalytic reaction) or a biological method (an isomerizing enzyme reaction) of using galactose as a main raw material (see PCT WO 2006/058092, Korean Patent Nos. 10-0964091 and 10-1368731). However, the price of lactose which is a basic raw material of galactose in the known production methods was unstable, depending on produced amounts, supply, and demand of raw milk and lactose in global markets, etc. Thus, there is a limitation in the stable supply of the raw material for tagatose production. Therefore, a new method capable of producing tagatose from a commonly used sugar (sucrose, glucose, fructose, etc.) as a raw material has been needed and studied, and the above-mentioned documents disclose a method of producing galactose, psicose, and tagatose from glucose, galactose, and fructose, respectively (Korean Patent Nos. 10-744479, 10-1057873, and 10-1550796).

Meanwhile, tagatose-6-phosphate kinase (EC 2.7.1.144) is known to produce ADP and D-tagatose 1,6-biphosphate from ATP and D-tagatose-6-phosphate as a substrate, as in the following [Reaction Scheme 1]. However, there have been no studies regarding whether the tagatose-6-phosphate kinase catalyzes conversion of fructose (D-fructose) into tagatose.

      1,6-biphosphate                   [Reaction Scheme 1]

Under this background, the present inventors have conducted extensive studies to develop an enzyme having activity to convert fructose into tagatose, and as a result, they found that tagatose-6-phosphate kinase (EC 2.7.1.144) has the ability to convert fructose into tagatose, thereby completing the present disclosure.

SUMMARY OF THE INVENTION

An object of the present disclosure is to provide a composition useful for the production of tagatose, comprising tagatose-6-phosphate kinase, a microorganism expressing the tagatose-6-phosphate kinase, or a culture of the microorganism.

Another object of the present disclosure is to provide a method of producing tagatose, comprising converting fructose into tagatose by contacting fructose with fructose-4-epimerase of the present disclosure, a microorganism expressing the fructose-4-epimerase, or a culture of the microorganism.

Hereinafter, other objects and advantages of the present disclosure will be described in more detail with reference to the following description along with the accompanying claims and drawings. Since contents that are not described in the present specification may be sufficiently recognized and inferred by those skilled in the art or similar art, a description thereof will be omitted.

DETAILED DESCRIPTION OF THE PREFERRED EMBODIMENTS

Figure 1:
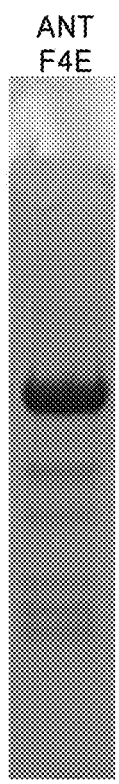
FIG. 1 shows a result of SDS-PAGE to analyze a molecular weight of tagatose-6-phosphate kinase (CJ_ANT_F4E) which was produced in and separated from a transformant according to one embodiment of the present disclosure.

Hereinafter, the present disclosure will be described in detail as follows. Meanwhile, each description and embodiment disclosed in this disclosure may be applied to other descriptions and embodiments. Further, all combinations of various elements disclosed in this disclosure fall within the scope of the present disclosure. Further, the scope of the present disclosure is not limited by the specific description described below.

To achieve objects of the present disclosure, an aspect of the present disclosure provides a composition for producing tagatose, comprising tagatose-6-phosphate kinase, a microorganism expressing the tagatose-6-phosphate kinase, or a culture of the microorganism.

The tagatose-6-phosphate kinase (EC 2.7.1.144) is known to produce ADP and D-tagatose 1,6-biphosphate from ATP and D-tagatose-6-phosphate as a substrate. For example, the tagatose-6-phosphate kinase may be any one without limitation as long as it is able to produce tagatose from fructose as a substrate. Specifically, the tagatose-6-phosphate kinase may have a conversion rate (conversion rate=weight of tagatose/initial weight of fructose*100) of 0.01% or more, specifically, 1% or more, and more specifically, 1.5% or more from fructose as a substrate into tagatose. More specifically, the conversion rate may be in the range from 0.01% to 40%, from 1% to 30%, from 1.5% to 25%, or from 1.5% to 23%.

Specifically, the composition may comprise one or more of a polypeptide consisting of an amino acid sequence of SEQ ID NO: 1, 3, 5, 7, 9, or 11 and a polypeptide having at least 80%, 90%, 95%, 97%, or 99% homology with the amino acid sequence of SEQ ID NO: 1, 3, 5, 7, 9, or 11. It is apparent that a polypeptide having the homology and an amino acid sequence exhibiting the efficacy (i.e., fructose-4-epimerization activity to convert into tagatose by epimerization at C4 position of fructose) corresponding to the protein consisting of the amino acid sequence of SEQ ID NO: 1, 3, 5, 7, 9, or 11 is also included in the scope of the present disclosure, although it has an amino acid sequence, of which a partial sequence is deleted, modified, substituted, or added. Further, a probe which may be produced from the known nucleotide sequence, for example, a polypeptide encoded by a polynucleotide which is hybridizable with a complementary sequence to all or a part of a nucleotide sequence encoding the polypeptide under stringent conditions may be also included without limitation, as long as it has the fructose-4-epimerization activity.

The present disclosure revealed that the 'tagatose-6-phosphate kinase' exhibits the fructose-4-epimerization activity to convert fructose into tagatose by epimerizing fructose at C4 position. In the present disclosure, therefore, the 'tagatose-6-phosphate kinase' may be used interchangeably with 'fructose-4-epimerase'.

As used herein, the term "stringent conditions" mean conditions under which specific hybridization between polynucleotides is allowed. These conditions depend on the length of the polynucleotide and the degree of complementation, and variables are well known in the art, and specifically described in a literature (e.g., J. Sambrook et al., infra). The stringent conditions may include, for example, conditions under which genes having high homology, 80% or higher homology, 90% or higher homology, 95% or higher homology, 97% or higher homology, 99% or higher homology are hybridized with each other and genes having homology lower than the above homology are not hybridized with each other, or ordinary washing conditions of Southern hybridization, i.e., washing once, specifically, twice or three times at a salt concentration and a temperature corresponding to 60° C., 1×SSC, 0.1% SDS, specifically, 60° C., 0.1×SSC, 0.1% SDS, and more specifically 68° C., 0.1× SSC, 0.1% SDS. The probe used in the hybridization may be a part of a complementary sequence of the nucleotide sequence. Such a probe may be produced by PCR using oligonucleotides produced based on the known sequence as primers and a DNA fragment containing these nucleotide sequences as a template. Further, those skilled in the art may adjust the temperature and the salt concentration of the washing solution according to factors such as the length of the probe, if necessary.

As used herein, the term "homology" refers to a percentage of identity between two polynucleotide or polypeptide moieties. Sequence homology from one moiety to another may be determined by a known technique in the art. For example, the homology may be determined by directly aligning the sequence information of two polynucleotide molecules or two polypeptide molecules, e.g., parameters such as score, identity, similarity, etc., using a computer program that is readily available and capable of aligning sequence information (e.g., BLAST 2.0). Additionally, the homology between polynucleotides may be determined by hybridizing the polynucleotides under a condition for forming a stable double-strand in the homologous regions followed by digesting the hybridized strand by a single-strand-specific nuclease to determine the size of digested fragments.

In one embodiment, the fructose-4-epimerase of the present disclosure may be an enzyme derived from a heat-resistant microorganism, for example, an enzyme derived from *Anaerolinea* sp., the genus of *Thermobifida*, the genus of *Thermoanaerobacter*, or a variant thereof, an enzyme derived from the genus of *Dictyoglomus* or a variant thereof, specifically, an enzyme derived from *Anaerolinea thermophila, Anaerolineae bacterium, Anaerolinea thermolimosa, Thermobifida halotolerans, Thermoanaerobacter indiensis*, or *Dictyoglomus thermophilum*, or a variant thereof, but is not limited thereto.

The fructose-4-epimerase of the present disclosure or a variant thereof is characterized by converting D-fructose into D-tagatose by epimerizing D-fructose at C4 position. It was revealed that the tagatose-6-phosphate kinase of the present disclosure has fructose-4-epimerase activity. The tagatose-6-phosphate kinase has been known to produce D-tagatose 1,6-biphosphate from D-tagatose 6-phosphate as a substrate. In other words, it was newly revealed that the tagatose-6-phosphate kinase has fructose-4-epimerase activity. Accordingly, one embodiment of the present disclosure relates to novel use of the tagatose-6-phosphate kinase including using the tagatose-6-phosphate kinase as the fructose-4-epimerase in the production of tagatose from fructose. Further, another embodiment of the present disclosure relates to a method of producing tagatose from fructose using the tagatose-6-phosphate kinase as the fructose-4-epimerase.

In one embodiment, the fructose-4-epimerase of the present disclosure may be an enzyme having high heat resistance. Specifically, the fructose-4-epimerase of the present disclosure may exhibit 50% to 100%, 60% to 100%, 70% to 100%, or 75% to 100% of its maximum activity at 50° C. to 70° C. More specifically, the fructose-4-epimerase of the present disclosure may exhibit 80% to 100% or 85% to 100% of its maximum activity at 55° C. to 60° C., 60° C. to 70° C., 65° C., 60° C., or 70° C.

Furthermore, the fructose-4-epimerase consisting of SEQ ID NO: 1 may be encoded by a nucleotide sequence of SEQ ID NO: 2; the fructose-4-epimerase consisting of SEQ ID NO: 3 may be encoded by a nucleotide sequence of SEQ ID NO: 4; the fructose-4-epimerase consisting of SEQ ID NO: 5 may be encoded by a nucleotide sequence of SEQ ID NO: 6; the fructose-4-epimerase consisting of SEQ ID NO: 7 may be encoded by a nucleotide sequence of SEQ ID NO: 8; the fructose-4-epimerase consisting of SEQ ID NO: 9 may be encoded by a nucleotide sequence of SEQ ID NO: 10; the fructose-4-epimerase consisting of SEQ ID NO: 11 may be encoded by a nucleotide sequence of SEQ ID NO: 12, but is not limited thereto.

The fructose-4-epimerase of the present disclosure or a variant thereof may be obtained by transforming a microorganism such as *E. coli* with DNA expressing the enzyme of the present disclosure or the variant thereof, e.g., a nucleotide of SEQ ID NO: 2, 4, 6, 8, 10, or 12, culturing the microorganism to obtain a culture, disrupting the culture, and then performing purification using a column, etc. The microorganism for transformation may include *Corynebacterium glutamicum*, *Aspergillus oryzae*, or *Bacillus subtilis*, in addition to *Escherichia coli*.

In a specific embodiment, the transformed microorganism may be *E. coli* BL21(DE3)/CJ_ANT_F4E (another name thereof is *E. coli* BL21(DE3)/pBT7-C-His-an1), *E. coli* BL21(DE3)/CJ_AB_F4E, or *E. coli* BL21(DE3)/CJ_DT_F4E, *E. coli* BL21(DE3)/CJ_ANTA_F4E, *E. coli* BL21(DE3)/CJ_TH_F4E, *E. coli* BL21(DE3)/CJ_TAI_F4E, and these microorganisms were deposited at the Korean Culture Center of Microorganisms which is an International Depositary Authority under the provisions of the Budapest Treaty with Accession Nos. KCCM11996P (date of deposit: Mar. 20, 2017), KCCM12093P (date of deposit: Aug. 11, 2017), KCCM12109P (date of deposit: Sep. 13, 2017), KCCM12232P (date of deposit: Mar. 23, 2018), KCCM12235P (date of deposit: Mar. 23, 2018), and KCCM12236P (date of deposit: Mar. 23, 2018). The fructose-4-epimerase used in the present disclosure may be provided by using a nucleic acid encoding the same.

As used herein, the term "nucleic acid" means that it encompasses DNA or RNA molecules, wherein nucleotides which are basic constituent units in the nucleic acid may include not only natural nucleotides but also analogues with modification of sugar or base (see: Scheit, Nucleotide Analogs, John Wiley, New York (1980); Uhlman and Peyman, Chemical Reviews, 90:543-584(1990)).

The nucleic acid of the present disclosure may be a nucleic acid encoding the polypeptide consisting of the amino acid sequence of SEQ ID NO: 1, 3, 5, 7, 9, or 11 of the present disclosure or a nucleic acid encoding a polypeptide having at least 80%, 90%, 95%, 97% or 99% homology with the fructose-4-epimerase of the present disclosure and having the fructose-4-epimerase activity. Specifically, the nucleic acid encoding the fructose-4-epimerase consisting of the amino acid sequence of SEQ ID NO: 1, 3, 5, 7, 9, or 11 may be a nucleic acid having at least 80%, 90%, 95%, 97%, 99% or 100% homology with the nucleotide sequence of SEQ ID NO: 2, 4, 6, 8, 10, or 12. It is also apparent that the nucleic acid of the present disclosure may include a nucleic acid which is translated into the fructose-4-epimerase of the present disclosure due to codon degeneracy or a nucleic acid which hybridizes with a nucleic acid consisting of a nucleotide sequence complementary to the nucleotide sequence of SEQ ID NO: 2, 4, 6, 8, 10, or 12 under stringent conditions and encodes the polypeptide having the fructose-4-epimerase activity of the present disclosure.

The microorganism expressing the fructose-4-epimerase which may be used in the present disclosure may be a microorganism including a recombinant vector including the nucleic acid. The vector may be operably linked to the nucleic acid of the present disclosure. As used herein, the term "operably linked" means that a nucleotide expression regulatory sequence and a nucleotide sequence encoding a desired protein are operably linked to each other to perform the general functions, thereby affecting expression of the encoding nucleotide sequence. The operable linkage to the vector may be produced using a genetic recombination technology known in the art, and the site-specific DNA cleavage and linkage may be produced using restriction enzymes and ligases known in the art.

As used herein, the term "vector" refers to any mediator for cloning and/or transferring of bases into an organism, such as a host cell. The vector may be a replicon that is able to bring the replication of combined fragments in which different DNA fragments are combined. Here, the term "replicon" refers to any genetic unit (e.g., plasmid, phage, cosmid, chromosome, virus) which functions as a self-unit of DNA replication in vivo, i.e., which is able to be replicated by self-regulation. As used herein, the term "vector" may include viral and non-viral mediators for introducing the bases into the organism, e.g., a host cell, in vitro, ex vivo, or in vivo, and may also include a minicircular DNA, a transposon such as Sleeping Beauty (Izsvak et al. J. Mol. Biol. 302:93-102 (2000)), or an artificial chromosome. Examples of the vector commonly used may include natural or recombinant plasmids, cosmids, viruses, and bacteriophages. For example, as a phage vector or cosmid vector, pWE15, M13, MBL3, MBL4, IXII, ASHII, APII, t10, t11, Charon4A, Charon21A, etc., may be used; and as a plasmid vector, those based on pBR, pUC, pBluescriptII, pGEM, pTZ, pCL, pET, etc., may be used. The vectors that may be used in the present disclosure are not particularly limited, but any known recombinant vector may be used.

Further, the vector may be a recombinant vector characterized by further including various antibiotic resistance genes. As used herein, the term "antibiotic resistance gene" refers to a gene having resistance against an antibiotic, and a cell having this gene survives in an environment treated with the corresponding antibiotic. Thus, the antibiotic resistance gene is used as a selectable marker during production of a large amount of plasmids in *E. coli*. The antibiotic resistance gene in the present disclosure is not a factor that greatly influences expression efficiency according to optimal combinations of vectors which is a key technology of the present disclosure, and thus an antibiotic resistance gene that is generally used as a selectable marker may be used without limitation. Specific examples may include a resistance gene against ampicilin, tetracyclin, kanamycin, chloroamphenicol, streptomycin, or neomycin.

The microorganism expressing the fructose-4-epimerase which may be used in the present disclosure may be obtained by a method of introducing the vector including the nucleic acid encoding the enzyme into a host cell, and a method of transforming the vector may be any method as long as it is able to introduce the nucleic acid into the cell. An appropriate standard technique known in the art may be selected and performed. Electroporation, calcium phosphate co-precipitation, retroviral infection, microinjection, a DEAE-dextran method, a cationic liposome method, and a heat shock method may be included, but is not limited thereto.

As long as the transformed gene may be expressed in the host cell, it may be integrated into and placed in the chromosome of the host cell, or it may exist extrachromosomally. Further, the gene includes DNA and RNA as a polynucleotide encoding a polypeptide, and any form may be used without limitation, as long as it may be introduced into the host cell and expressed therein. For example, the gene may be introduced into the host cell in the form of an expression cassette, which is a polynucleotide construct including all elements required for its autonomous expression. Commonly, the expression cassette includes a promoter operably linked to the gene, transcriptional termination signals, ribosome binding sites, and translation termination signals. The expression cassette may be in the form of a self-replicable expression vector. Also, the gene as it is or in the form of a polynucleotide construct may be introduced into the host cell and operably linked to sequences required for expression in the host cell.

The microorganism of the present disclosure may include either a prokaryotic microorganism or a eukaryotic microorganism, as long as it is a microorganism capable of producing the fructose-4-epimerase of the present disclosure by including the nucleic acid of the present disclosure or the recombinant vector of the present disclosure. For example, the microorganism may include microorganism strains belonging to the genus *Escherichia*, the genus *Erwinia*, the genus *Serratia*, the genus *Providencia*, the genus *Corynebacterium*, and the genus *Brevibacterium*, and specifically, it may be *E. coli* or *Corynebacterium glutamicum*, but is not limited thereto. Specific examples of the microorganism may include *E. coli* BL21(DE3)/CJ_ANT_F4E, *E. coli* BL21(DE3)/CJ_AB_F4E, *E. coli* BL21(DE3)/CJ_DT_F4E, *E. coli* BL21(DE3)/CJ_ANTA_F4E, *E. coli* BL21(DE3)/CJ_TH_F4E, or *E. coli* BL21(DE3)/CJ_TAI_F4E.

The microorganism of the present disclosure may include any microorganism capable of expressing the fructose-4-epimerase of the present disclosure according to various known methods, in addition to introduction of the nucleic acid or the vector.

The culture of the microorganism of the present disclosure may be produced by culturing, in a medium, the microorganism capable of expressing the tagatose-6-phosphate kinase of the present disclosure.

As used herein, the term "culturing" means that the microorganism is allowed to grow under appropriately controlled environmental conditions. The culturing process of the present disclosure may be carried out according to an appropriate medium and culture conditions known in the art.

The culturing process may be easily adjusted by those skilled in the art according to the strain to be selected. The step of culturing the microorganism may be, but is not particularly limited to, carried out by a known batch process, a continuous process, or a fed batch process. With regard to the culture conditions, a proper pH (e.g., pH 5 to 9, specifically pH 7 to 9) may be adjusted using a basic compound (e.g., sodium hydroxide, potassium hydroxide, or ammonia) or an acidic compound (e.g., phosphoric acid or sulfuric acid), but is not particularly limited thereto. Additionally, an antifoaming agent such as fatty acid polyglycol ester may be added during the culturing process to prevent foam generation. Additionally, oxygen or an oxygen-containing gas may be injected into the culture in order to maintain an aerobic state of the culture; or nitrogen, hydrogen, or carbon dioxide gas may be injected without the injection of a gas in order to maintain an anaerobic or microaerobic state of the culture. The culture temperature may be maintained from 25° C. to 40° C., and specifically, from 30° C. to 37° C., but is not limited thereto. The culturing may be continued until the desired amount of useful materials is obtained, and specifically for about 0.5 hours to about 60 hours, but is not limited thereto. Furthermore, the culture medium to be used may include, as sugar sources, sugars and carbohydrates (e.g., glucose, sucrose, lactose, fructose, maltose, molasses, starch, and cellulose), oils and fats (e.g., soybean oil, sunflower oil, peanut oil, and coconut oil), fatty acids (e.g., palmitic acid, stearic acid, and linoleic acid), alcohols (e.g., glycerol and ethanol), and organic acids (e.g., acetic acid). These substances may be used individually or in a mixture, but are not limited thereto. Nitrogen sources may include nitrogen-containing organic compounds (e.g., peptone, yeast extract, meat extract, malt extract, corn steep liquor, soybean meal, and urea) or inorganic compounds (e.g., ammonium sulfate, ammonium chloride, ammonium phosphate, ammonium carbonate, and ammonium nitrate). These nitrogen sources may also be used individually or in a mixture, but are not limited thereto. Phosphorus sources may include potassium dihydrogen phosphate, dipotassium hydrogen phosphate, or the corresponding sodium salts. These phosphorus sources may also be used individually or in a mixture, but are not limited thereto. The culture medium may include essential growth stimulators, such as metal salts (e.g., magnesium sulfate or iron sulfate), amino acids, and vitamins.

The composition for producing tagatose of the present disclosure may further include fructose.

The composition for producing tagatose of the present disclosure may include tagatose-6-phosphate kinase having fructose-4-epimerization activity to directly convert fructose into tagatose, a microorganism expressing the tagatose-6-phosphate kinase, or a culture of the microorganism, the composition characterized by not including other enzymes than fructose as a substrate.

For example, the composition for producing tagatose of the present disclosure may be characterized by not including, for example, α-glucan phosphorylase, starch phosphorylase, maltodextrin phosphorylase, or sucrose phosphorylase, a microorganism expressing thereof, or a culture of the microorganism;

glucokinase, a microorganism expressing the glucokinase, or a culture of the microorganism;

tagatose-6-phosphate phosphatase, a microorganism expressing the tagatose-6-phosphate phosphatase, or a culture of the microorganism; and/or α-amylase, pullulanase, glucoamylase, sucrase, or isoamylase; a microorganism expressing the amylase, pullulanase, glucoamylase, sucrase, or isoamylase; or a culture of the microorganism expressing the amylase, pullulanase, glucoamylase, sucrase, or isoamylase.

The composition for producing tagatose of the present disclosure may further include any suitable excipient commonly used in the corresponding composition for producing tagatose. The excipient may include, for example, a preservative, a wetting agent, a dispersing agent, a suspending agent, a buffer, a stabilizing agent, an isotonic agent, etc., but is not limited thereto.

The composition for producing tagatose of the present disclosure may further include a metal. In one embodiment, the metal of the present disclosure may be a metal containing a divalent cation. Specifically, the metal of the present disclosure may be magnesium, nickel, or manganese (Mn). More specifically, the metal of the present disclosure may be a metal ion or a metal salt, and much more specifically, the metal salt may be $MgCl_2$, $MgSO_4$, $NiSO_4$, $NiCl_2$, $MnCl_2$, or $MnSO_4$.

Still another aspect of the present disclosure provides a method of producing tagatose, comprising converting fructose into tagatose by contacting fructose (D-fructose with fructose-4-epimerase of the present disclosure, the microorganism expressing the fructose-4-epimerase, or the culture of the microorganism.

In one embodiment, the contacting of the present disclosure may be performed under conditions of pH 5.0 to pH 9.0 and 30° C. to 80° C. and/or for 0.5 hours to 48 hours.

Specifically, the contacting of the present disclosure may be performed under a condition of pH 6.0 to pH 9.0 or pH 7.0 to pH 9.0. Further, the contacting of the present disclosure may be performed under a temperature condition of 35° C. to 80° C., 40° C. to 80° C., 45° C. to 80° C., 50° C. to 80° C., 55° C. to 80° C., 60° C. to 80° C., 30° C. to 70° C., 35° C. to 70° C., 40° C. to 70° C., 45° C. to 70° C., 50° C. to 70° C., 55° C. to 70° C., 60° C. to 70° C., 30° C. to 65° C., 35° C. to 65° C., 40° C. to 65° C., 45° C. to 65° C., 50° C. to 65° C., 55° C. to 65° C., 30° C. to 60° C., 35° C. to 60° C., 40° C. to 60° C., 45° C. to 60° C., 50° C. to 60° C. or 55° C. to 60° C. Furthermore, the contacting of the present disclosure may be performed for 0.5 hours to 36 hours, 0.5 hours to 24 hours, 0.5 hours to 12 hours, 0.5 hours to 6 hours, 1 hour to 48 hours, 1 hour to 36 hours, 1 hour to 24 hours, 1 hour to 12 hours, 1 hour to 6 hours, 3 hours to 48 hours, 3 hours to 36 hours, 3 hours to 24 hours, 3 hours to 12 hours, 3 hours to 6 hours, 6 hours to 48 hours, 6 hours to 36 hours, 6 hours to 24 hours, 6 hours to 12 hours, 9 hours to 48 hours, 9 hours to 36 hours, 9 hours to 24 hours, or 9 hours to 12 hours.

In one embodiment, the contacting of the present disclosure may be performed in the presence of a metal.

In the method of producing tagatose of the present disclosure, the fructose-4-epimerase of the present disclosure, the microorganism expressing the fructose-4-epimerase, the culture of the microorganism, the metal, the metal ion, and the metal salt are the same as those in the above-described embodiment.

The production method of the present disclosure may further include separating and/or purifying the produced tagatose. The separation and/or purification may be a method commonly used in the art. Non-limiting examples may include dialysis, precipitation, adsorption, electrophoresis, ion exchange chromatography, fractional crystallization, etc. The purification method may be performed only by a single method or by two or more methods.

In addition, the production method of the present disclosure may further include the step of performing decolorization and/or desalination, before or after the separation and/or purification step(s). By performing the decolorization and/or desalination, it is possible to obtain tagatose with higher quality.

In still another embodiment, the production method of the present disclosure may further include the step of performing crystallization of tagatose, after the step of converting into tagatose of the present disclosure, performing the separation and/or purification, or performing the decolorization and/or desalination. The crystallization may performed by a crystallization method commonly used. For example, the crystallization may performed by cooling crystallization.

In still another embodiment, the production method of the present disclosure may further include the step of concentrating tagatose, before the crystallization. The concentrating may increase the crystallization efficiency.

In still another embodiment, the production method of the present disclosure may further include the step of contacting unreacted fructose with the enzyme of the present disclosure, the microorganism expressing the enzyme, or the culture of the microorganism after separation and/or purification, the step of reusing a crystal-separated mother solution in the separation and/or purification after the crystallization of the present disclosure, or a combination thereof. The additional steps are economically advantageous in that tagatose may be obtained with higher yield, and the amount of fructose to be discarded may be reduced.

Hereinafter, the present disclosure will be described in more detail with reference to Examples. However, the following Examples of the present disclosure are merely an example of the present disclosure, and the content of the present disclosure is not limited thereto. It will be apparent to those skilled in the art that these Examples are for the purpose of illustrating the present disclosure in more detail and the scope of the present disclosure as set forth in the appended claims is not limited by these Examples.

Example 1: Production of Tagatose-6-Phosphate Kinase and Evaluation of its Activity Example 1-1: Production of Recombinant Expression Vectors and Transformants Including Tagatose-6-Phosphate Kinase Gene To provide a novel heat-resistant fructose-4-epimerase, information of tagatose-6-phosphate kinase genes derived from two kinds of *Anaerolinea thermophile* was obtained to prepare vectors expressible in *E. coli* and transformed microorganisms (transformants).

In detail, a nucleotide sequence of tagatose-6-phosphate kinase was selected from nucleotide sequences of *Anaerolinea thermophile*, which are registered in KEGG (Kyoto Encyclopedia of Genes and Genomes), and based on an amino acid sequence (SEQ ID NO: 1) and a nucleotide sequence (SEQ ID NO: 2) and an amino acid sequence (SEQ ID NO: 7) and a nucleotide sequence (SEQ ID NO: 8) of *Anaerolinea thermophile*, recombinant expression vectors prepared by inserting into pBT7-C-His which is a vector expressible in *E. coli* were synthesized in Bioneer Corp. To use the recombinant expression vector, PCR was performed using genomic DNA of *Anaerolinea thermophile* and primer 1: ATATACATAT-GATGTTCGGCTCGCCTGCTCCCCTGCTG (SEQ ID NO: 13) and primer 2: TGGTGCTCG-AGCCCGCACGCCGCAGCGTAATCTTCCAG (SEQ ID NO: 14) under conditions of denaturation at 94° C. for 2 minutes, followed by 35 cycles of denaturation at 94° C. for 30 seconds, annealing at 60° C. for 30 seconds, elongation at 72° C. for 2 minutes, and then elongation at 72° C. for 5 minutes.

To induce protein expression, each vector was transformed into BL21(DE3) which is a strain for expression in *E. coli*, and designated as *E. coli* BL21(DE3)/CJ_ANT_F4E and *E. coli* BL21(DE3)/CJ_ANTA_F4E, respectively. *E. coli* BL21(DE3)/CJ_ANT_F4E and *E. coli* BL21(DE3)/CJ_ANTA_F4E were deposited under the provisions of the Budapest Treaty with Accession No. KCCM11996P on Mar. 20, 2017, and Accession No. KCCM12232P on Mar. 23, 2018, respectively.

Example 1-2: Production and Purification of Recombinant Enzymes

To produce recombinant enzymes, each of *E. coli* BL21 (DE3)/CJ_ANT_F4E and *E. coli* BL21(DE3)/CJ_ANTA_F4E which are the transformants produced in Example 1-1 was seeded in a culture tube containing 5 mL of an LB liquid medium with ampicillin, and then seed culture was performed in a shaking incubator at 37° C. until absorbance at 600 nm reached 2.0. Each of the cultures obtained by the seed culture was seeded in a culture flask containing a liquid medium containing LB (Lysogeny broth) and lactose which is a protein expression regulator, and then main culture was performed. During the culture, a shaking speed was maintained at 180 rpm and a culture temperature was maintained at 37° C. Each culture was centrifuged at 8,000 rpm and 4° C. for 20 minutes to recover cells. The recovered cells were washed with 50 mM Tris-HCl (pH 8.0) buffer twice and re-suspended in 50 mM $NaH_2PO_4$ (pH 8.0) buffer containing 10 mM imidazole and 300 mM NaCl. The re-suspended cells were disrupted using a sonicator. Cell lysates were centrifuged at 13,000 rpm and 4° C. for 20 minutes to obtain only supernatants. Each supernatant was purified by His-tag affinity chromatography, and 10 column volumes of 50 mM $NaH_2PO_4$ (pH 8.0) buffer containing 20 mM imidazole and 300 mM NaCl was applied to remove non-specifically bound proteins. Next, 50 mM $NaH_2PO_4$ (pH 8.0) buffer containing 250 mM imidazole and 300 mM NaCl was further applied to perform elution. Dialysis was performed using 50 mM Tris-HCl (pH 8.0) buffer to obtain two kinds of enzymes (CJ_ANT_F4E, CJ_ANTA_F4E) for enzyme characterization. As a result, it was confirmed that the purified recombinant fructose-4-epimerase was subjected to SDS-PAGE analysis, and CJ_ANT_F4E was about 47 kDa (FIG. 1).

Example 1-3: Evaluation of Activity to Convert Fructose into Tagatose

To measure activities of the enzymes obtained in Example 1-2, 30% by weight of fructose was used, and 50 mM Tris-HCl (pH 8.0), 1 mM $CoSO_4$, and 20 mg/mL of purified enzyme separated in Example 1-2 were added thereto, and allowed to react at 60° C. for 2 hours. Concentrations of tagatose converted by the fructose-4-epimerases, CJ_ANT_F4E and CJ_ANTA_F4E, and conversion rates from fructose to tagatose were examined, and as a result, CJ_ANT_F4E showed a conversion rate of 16.1%, and CJ_ANTA_F4E showed a conversion rate of 21.9%. These conversion rates were calculated by the following equation: conversion rate=production amount of tagatose/concentration of fructose substrate×100

Figure 2:
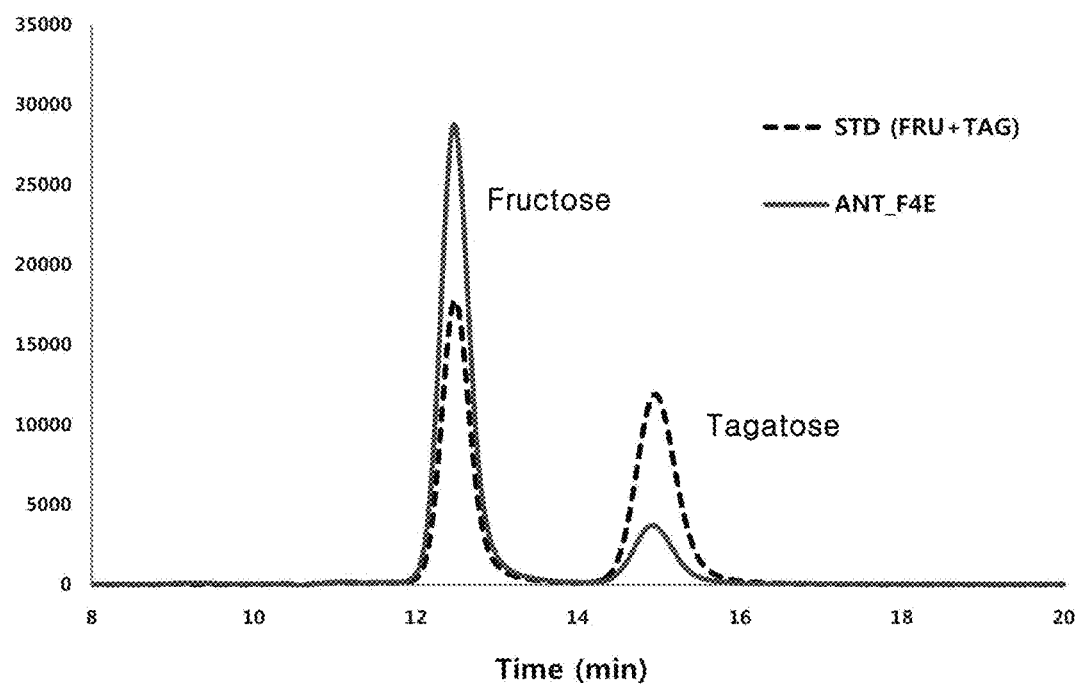
FIG. 2 is a result of HPLC chromatography showing that tagatose-6-phosphate kinase (CJ_ANT_F4E) prepared in one embodiment of the present disclosure has fructose-4-epimerase activity.
Figure 10:
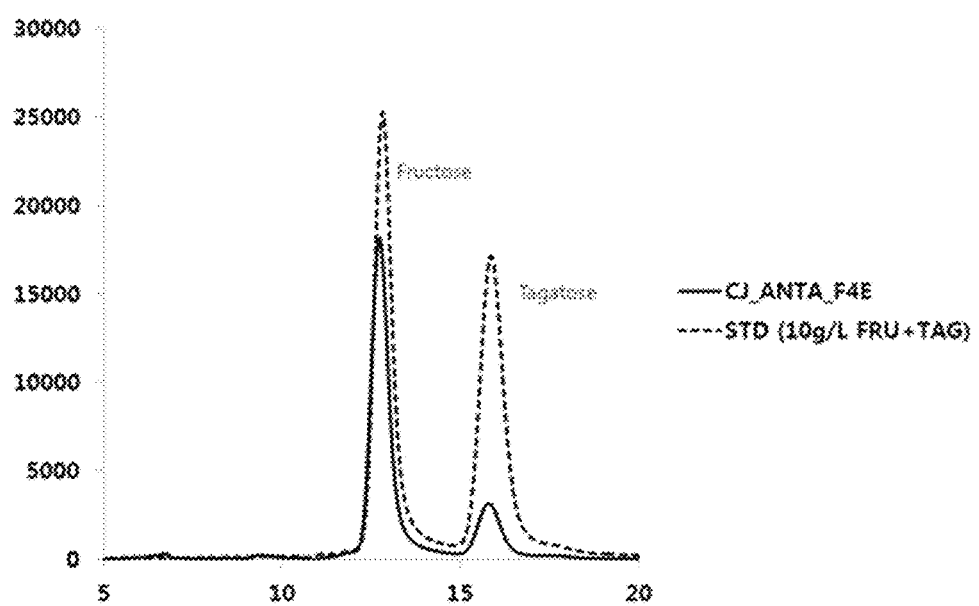
FIG. 10 is a result of HPLC chromatography showing that tagatose-6-phosphate kinase (CJ_ANTA_F4E) prepared in one embodiment of the present disclosure has fructose-4-epimerase activity.

Further, fructose remaining after reaction and a product tagatose were quantified by HPLC. Shodex Sugar SP0810 was used as a column, and a temperature of the column was 80° C., and water as a mobile phase was applied at a flow rate of 1 mL/min. In FIGS. 2 and 10, a peak that represents the reaction of the enzyme using fructose as a substrate was detected and quantified by HPLC chromatography.

Example 1-4: Effect of Temperature on Fructose-4-Epimerisation Activity

Figure 3:
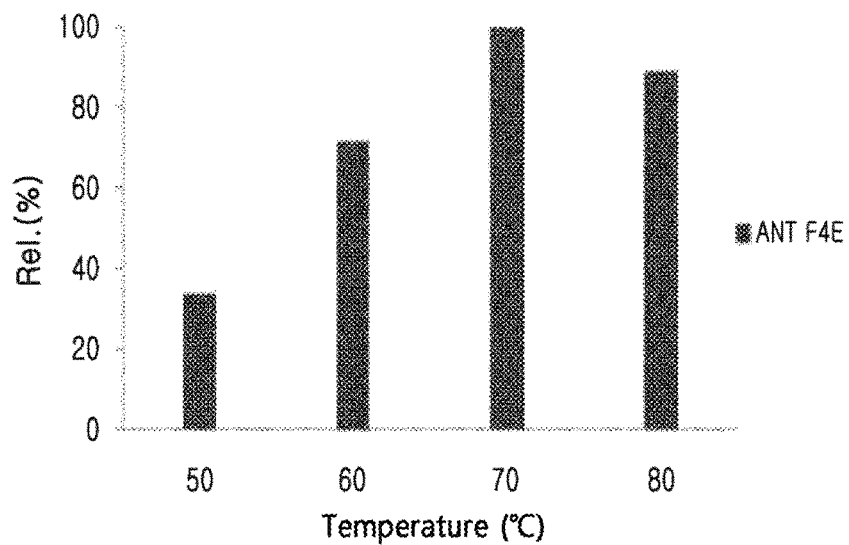
FIG. 3 is a graph showing fructose-4-epimerization activity of tagatose-6-phosphate kinase (CJ_ANT_F4E) prepared in one embodiment of the present disclosure according to temperature changes.

To examine an effect of temperature on the epimerization activities of the enzymes of the present disclosure, each 1 mg/mL of the purified enzymes produced in Example 1-2 was added to 50 mM Tris HCl (pH 8.0) buffer containing fructose, and allowed to react at 50° C. to 80° C. for 3 hours. Tagatose in each of the reacted solutions was quantified by HPLC. As a result, CJ_ANT_F4E enzyme of the present disclosure showed its maximum activities at 70° C. (FIG. 3).

Example 2: Example 2: Production of Tagatose-6-Phosphate Kinase and Evaluation of its Activity

Example 2-1: Production of Recombinant Expression Vector and Transformant Including Tagatose-6-Phosphate Kinase Gene The present inventors obtained Information of a tagatose-6-phosphate kinase gene derived from *Anaerolineae bacterium* Taxon ID: 2654588098, and prepared a recombinant vector expressible in *E. coli* and a transformed microorganism.

More specifically, a nucleotide sequence of tagatose-6-phosphate kinase was selected from a nucleotide sequence of *Anaerolineae bacterium*, which is registered in KEGG (Kyoto Encyclopedia of Genes and Genomes) and ENA (European Nucleotide Archive), and based on an amino acid sequence (SEQ ID NO: 3) and a nucleotide sequences (SEQ ID NO: 4) of tagatose-6-phosphate kinase CJ_AB_F4E derived from *Anaerolineae bacterium*, pBT7-C-His-CJ_AB_F4E which is a recombinant expression vector containing the nucleotide sequence of the enzyme and expressible in *E. coli* was produced (Bioneer Corp., Korea).

The recombinant vector was transformed into *E. coli* BL21(DE3) by heat shock transformation (Sambrook and Russell: Molecular cloning, 2001), and frozen and stored in 50% glycerol. The transformant was designated as *E. coli* BL21(DE3)/CJ_AB_F4E, and deposited at the Korean Culture Center of Microorganisms (KCCM) which is an international depositary authority under the provisions of the Budapest Treaty on Aug. 11, 2017 with Accession No. KCCM12093P.

Example 2-2: Production and Purification of Recombinant Enzyme

To obtain a recombinant enzyme of the present disclosure from *E. coli* BL21(DE3)/CJ_AB_F4E which is the transformant produced in Example 2-1, the transformant was seeded in a culture tube containing 5 mL of an LB liquid medium with ampicillin antibiotic, and then seed culture was performed in a shaking incubator at 37° C. until absorbance at 600 nm reached 2.0. The culture obtained by the seed culture was seeded in a culture flask containing a liquid medium containing LB and lactose which is a protein expression regulator, and then main culture was performed. The seed culture and the main culture were performed under conditions of 180 rpm and 37° C. Then, the culture was centrifuged at 8,000 rpm and 4° C. for 20 minutes to recover cells. The recovered cells were washed with 50 mM Tris-HCl (pH 8.0) buffer twice and re-suspended in 50 mM NaH$_2$PO$_4$ (pH 8.0) buffer containing 10 mM imidazole and 300 mM NaCl. The re-suspended cells were disrupted using a sonicator. A cell lysate was centrifuged at 13,000 rpm and 4° C. for 20 minutes to take only a supernatant. The supernatant was purified by His-tag affinity chromatography, and 10 column volumes of 50 mM NaH$_2$PO$_4$ (pH 8.0) buffer containing 20 mM imidazole and 300 mM NaCl was applied to remove non-specifically bound proteins. Next, 50 mM NaH$_2$PO$_4$ (pH 8.0) buffer containing 250 mM imidazole and 300 mM NaCl was further applied to perform elution. Dialysis was performed using 50 mM Tris-HCl (pH 8.0) buffer to obtain CJ_AB_F4E which is a purified enzyme for enzyme characterization.

Example 2-3: Evaluation of Activity of Recombinant Enzyme to Convert Fructose into Tagatose To measure activity of CJ_AB_F4E which is the recombinant enzyme of the present disclosure obtained in Example 2-2, 50 mM Tris-HCl (pH 8.0), 1 mM NiSO$_4$, and 20 mg/mL of CJ_AB_F4E were added to 30% by weight of fructose, and allowed to react at 60° C. for 10 hours.

Figure 4:
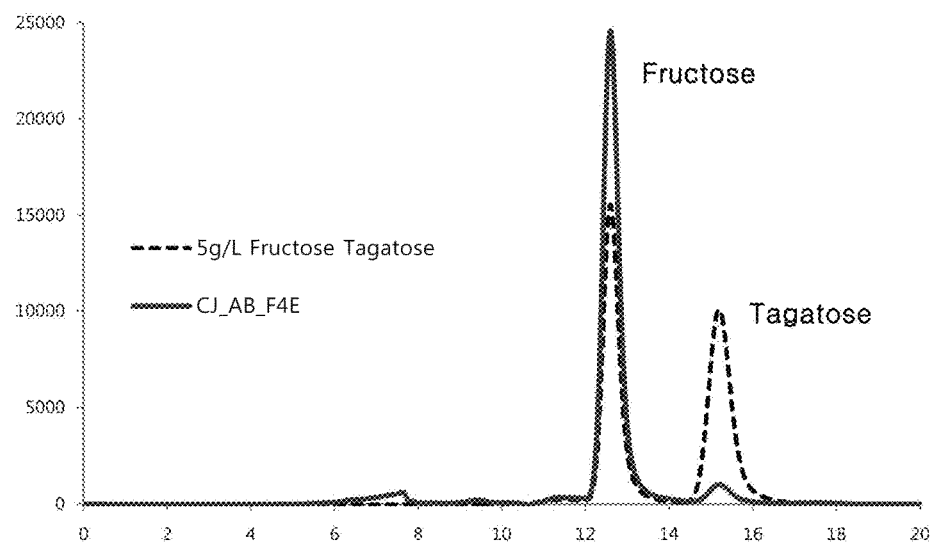
FIG. 4 is a result of HPLC chromatography showing that tagatose-6-phosphate kinase CJ_AB_F4E prepared in one embodiment of the present disclosure has fructose-4-epimerase activity.

Further, fructose remaining after reaction and a product tagatose were quantified by HPLC. HPLC was performed by using Shodex Sugar SP0810 as a column, and a temperature of the column was 80° C., and water as a mobile phase was applied at a flow rate of 1 mL/min (FIG. 4).

As a result, it was confirmed that the conversion rate from fructose into tagatose by the enzyme of the present disclosure was 5.1%.

Example 2-4: Examination of Activity of Recombinant Enzyme According to Temperature Change To examine an effect of temperature on the fructose-4-epimerization activity of the recombinant enzyme CJ_AB_F4E prepared in Example 2-2, 1 mg/mL of CJ_AB_F4E was added to 50 mM Tris HCl (pH 8.0) buffer containing 10% by weight of fructose, and allowed to react at different temperatures of 45° C., 50° C., 55° C., 60° C., and 70° C. for 3 hours. Tagatose in each of the reacted solutions was quantified by HPLC.

Figure 5:
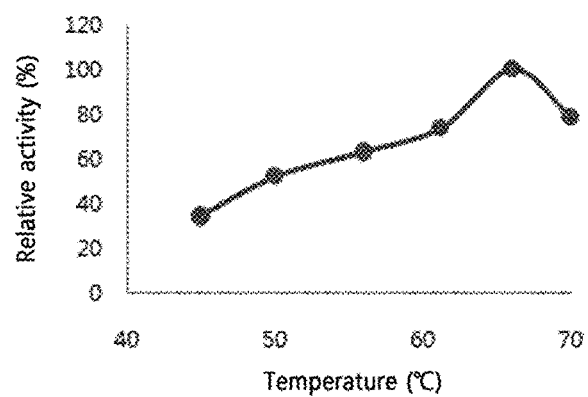
FIG. 5 is a graph showing fructose-4-epimerization activity of tagatose-6-phosphate kinase CJ_AB_F4E prepared in one embodiment of the present disclosure according to temperature changes.

As a result, CJ_AB_F4E showed its maximum activity at 65° C., and CJ_AB_F4E maintained 50% or more of its maximum activity at 50° C. to 70° C. (FIG. 5).

Example 2-5: Examination of Activity of Recombinant Enzyme According to Addition of Metal Ion The known isomerases, e.g., glucose isomerase and arabinose isomerase, and epimerases, e.g., psicose 3-epimerase are known to require metal ions. Therefore, it was examined whether metal ions affect the fructose-4-epimerization activity of the recombinant enzyme CJ_AB_F4E prepared in Example 2-2.

More specifically, 2 mg/mL of CJ_AB_F4E and each 1 mM of various metal ions, NiSO$_4$, CaCl$_2$, ZnSO$_4$, MgSO$_4$, MnSO$_4$, FeSO$_4$, CuSO$_4$, or (NH$_4$)$_2$SO$_4$ were added to 50 mM Tris HCl (pH 8.0) buffer containing 10% by weight of fructose to measure the enzyme activity. Non-treatment of the metal ions was determined as a control group. Tagatose in each of the reacted solutions was quantified by HPLC.

Figure 6:
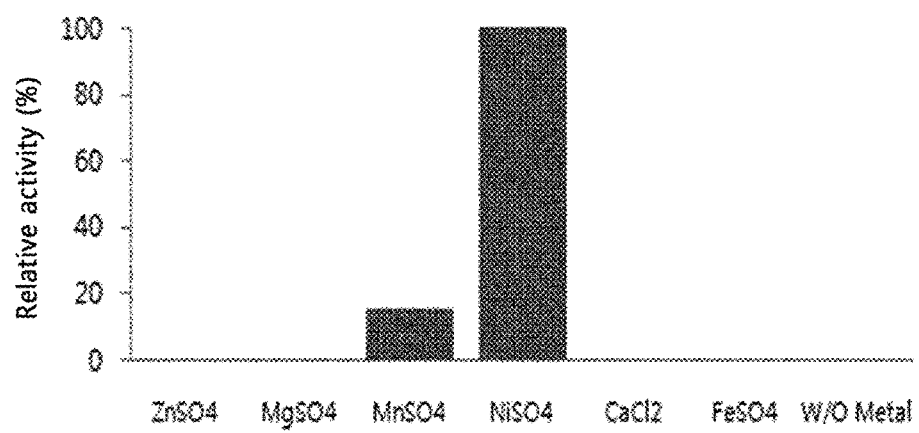
FIG. 6 is a graph showing fructose-4-epimerization activity of tagatose-6-phosphate kinase CJ_AB_F4E prepared in one embodiment of the present disclosure according to addition of metals.

As a result, the activity of CJ_AB_F4E of the present disclosure was increased by addition of MnSO4, or NiSO4, indicating that CJ_AB_F4E zequires metal ions such as manganese ion or nickel ion. In particular, CJ_AB_F4E showed its maximum activity when NiSO$_4$ was added (FIG. 6).

Example 3: Production of Tagatose-6-Phosphate Kinase and Evaluation of its Activity

Example 3-1: Production of Recombinant Vector and Recombinant Microorganism Including Tagatose-6-Phosphate Kinase Gene To identify a novel heat-resistant fructose-4-epimerase, information of tagatose-6-phosphate kinase gene derived from *Dictyoglomus thermophilum* DSM 3960 was obtained to prepare a vector expressible in *E. coli* and a transformed microorganism.

In detail, a nucleotide sequence of tagatose-6-phosphate kinase was selected from a nucleotide sequence of *Dictyoglomus thermophilum*, which is registered in KEGG (Kyoto Encyclopedia of Genes and Genomes), and based on an amino acid sequence (SEQ ID NO: 5) and a nucleotide sequence (SEQ ID NO: 6) of the tagatose-6-phosphate kinase CJ_DT_F4E derived from *Dictyoglomus thermophilum*, pBT7-C-His-CJ_DT_F4E which is a recombinant expression vector containing the nucleotide sequence of the enzyme and expressible in *E. coli* was synthesized (Bioneer Corp., Korea).

The recombinant vector was transformed into *E. coli* BL21(DE3) by heat shock transformation (Sambrook and Russell: Molecular cloning, 2001) to prepare a recombinant microorganism, which was then frozen and stored in 504 glycerol. The recombinant microorganism was designated as *E. coli* BL21(DE3)/CJ_DT_F4E, and deposited at the Korean Culture Center of Microorganisms (KCCM) which is an international depositary authority under the provisions of the Budapest Treaty on Sep. 13, 2017 with Accession No. KCCM12109P.

Example 3-2: Production and Purification of Recombinant Enzyme

To produce recombinant enzyme CJ_DT_F4E from *E. coli* BL21(DE3)/CJ_DT_F4E which is the recombinant microorganism produced in Example 3-1, the recombinant microorganism was seeded in a culture tube containing 5 mL of an LB liquid medium with ampicillin antibiotic, and then seed culture was performed in a shaking incubator at 37° C. until absorbance at 600 nm reached 2.0. The culture obtained by the seed culture was seeded in a culture flask containing a liquid medium containing LB and lactose which is a protein expression regulator, and then main culture was performed. The seed culture and the main culture were performed under conditions of 180 rpm and 37° C. Then, the culture was centrifuged at 8,000 rpm and 4° C. for 20 minutes to recover cells. The recovered cells were washed with 50 mM Tris-HCl (pH 8.0) buffer twice and suspended in 50 mM NaH$_2$PO$_4$ (pH 8.0) buffer containing 10 mM imidazole and 300 mM NaCl. The suspended cells were disrupted using a sonicator. Cell lysates were centrifuged at 13,000 rpm and 4° C. for 20 minutes to take only a supernatant. The supernatant was purified by His-tag affinity chromatography, and 10 column volumes of 50 mM NaH$_2$PO$_4$ (pH 8.0) buffer containing 20 mM imidazole and 300 mM NaCl was applied to remove non-specifically bound proteins. Next, 50 mM NaH$_2$PO$_4$ (pH 8.0) buffer containing 250 mM imidazole and 300 mM NaCl was further applied to perform elution. Dialysis was performed using 50 mM Tris-HCl (pH 8.0) buffer to obtain CJ_DT_F4E which is a purified enzyme for enzyme characterization.

Example 3-3: Evaluation of Activity of Recombinant Enzyme to Convert Fructose into Tagatose To measure activity of CJ_DT_F4E which is the recombinant enzyme obtained in Example 3-2, 50 mM Tris-HCl (pH 8.0), 1 mM MnSO$_4$, and 5 mg/mL of CJ_DT_F4E were added to 30% by weight of fructose, and allowed to react at 60° C. for 10 hours.

Figure 7:
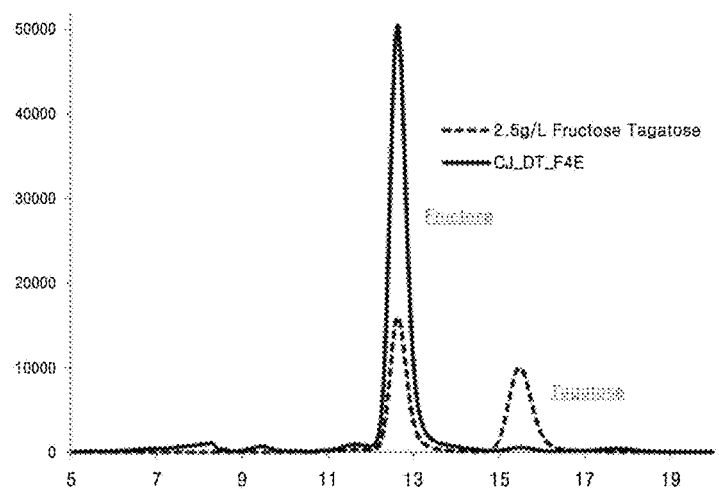
FIG. 7 is a result of HPLC chromatography showing that tagatose-6-phosphate kinase CJ_DT_F4E prepared in one embodiment of the present disclosure has fructose-4-epimerase activity.

Further, fructose remaining after reaction and a product tagatose were quantified by HPLC. HPLC was performed by using Shodex Sugar SP0810 as a column, and a temperature of the column was 80° C., and water as a mobile phase was applied at a flow rate of 1 mL/min (FIG. 7).

As a result, it was confirmed that the conversion rate from fructose into tagatose by the recombinant enzyme CJ_DT_F4E was 2%.

Example 3-4: Examination of Activity of Recombinant Enzyme According to Temperature To examine an effect of temperature on the fructose-4-epimerization activity of the recombinant enzyme CJ_DT_F4E obtained in Example 3-2, 5 mg/mL of CJ_DT_F4E was added to 50 mM Tris HCl (pH 8.0) buffer containing 5% by weight of fructose, and allowed to react at 40° C., 50° C., 55° C., 60° C. and 70° C. for 5 hours. Tagatose in each of the reacted solutions was quantified by HPLC.

Figure 8:
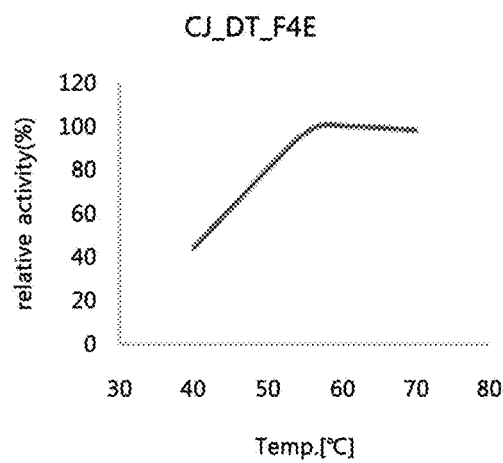
FIG. 8 is a graph showing fructose-4-epimerization activity of tagatose-6-phosphate kinase CJ_DT_F4E prepared in one embodiment of the present disclosure according to temperature changes.

As a result, CJ_DT_F4E showed its maximum activity at 60° C., and showed 80% or more of its maximum activity at 50° C. to 70° C. and 95% or more of its maximum activity at 55° C. to 70° C. (Table 1, FIG. 8).

TABLE 1

| Relative activity (%) at each temperature | |
|---|---|
| Section | CJ_DT_F4E |
| 40° C. | 44.0 |
| 50° C. | 80.3 |
| 55° C. | 98.9 |
| 60° C. | 100.0 |
| 70° C. | 98.2 |

Example 3-5: Examination of Activity of Recombinant Enzyme According to Addition of Metal It was examined whether metals affect the fructose-4-epimerization activity of the recombinant enzyme CJ_DT_F4E prepared in Example 3-2.

In detail, 5 mg/mL of CJ_DT_F4E and 1 mM of a metal ion (MgSO$_4$ or MnSO$_4$) were added to 50 mM Tris HCl (pH 8.0) buffer containing 5% by weight of fructose, and then enzyme activity was measured. Non-treatment of the metal ions was determined as a control group (w/o). Tagatose in each of the reacted solutions was quantified by HPLC.

Figure 9:
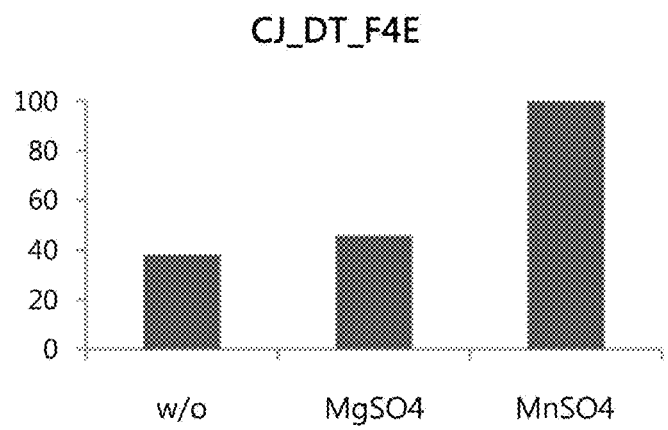
FIG. 9 is a graph showing fructose-4-epimerization activity of tagatose-6-phosphate kinase CJ_DT_F4E prepared in one embodiment of the present disclosure according to addition of metals.

As a result, the activity of CJ_DT_F4E was increased by addition of MnSO$_4$ or MgSO$_4$, indicating that manganese ion or magnesium ion (or a salt thereof) is able to increase the fructose-4-epimerization activity of CJ_DT_F4E (FIG. 9). In particular, it was confirmed that the activity of CJ_DT_F4E was increased about 2.5 times or more by addition of MnSO$_4$, as compared with the control group (FIG. 9).

Example 4: Production of Tagatose-6-Phosphate Kinase and Evaluation of its Activity

Example 4-1: Production of Recombinant Vector and Recombinant Microorganism Including Tagatose-6-Phosphate Kinase Gene To identify a novel heat-resistant fructose-4-epimerase, information of a tagatose-6-phosphate kinase gene derived from *Thermobifida halotolerans* was obtained to prepare a recombinant vector expressible in *E. coli* and a transformed recombinant microorganism.

Specifically, a nucleotide sequence of tagatose-6-phosphate kinase was selected from a nucleotide sequence of *Thermobifida halotolerans*, which is registered in KEGG (Kyoto Encyclopedia of Genes and Genomes), and based on an amino acid sequence (SEQ ID NO: 9) and a nucleotide sequences (SEQ ID NO: 10) of the tagatose-6-phosphate kinase CJ-TH_F4E derived from *Thermobifida halotolerans*, pBT7-C-His-CJ_TH_F4E which is a recombinant expression vector containing the nucleotide sequence of the enzyme and expressible in *E. coli* was synthesized (Bioneer Corp., Korea).

The recombinant vector was transformed into *E. coli* BL21(DE3) by heat shock transformation (Sambrook and Russell: Molecular cloning, 2001) to prepare a recombinant microorganism, and frozen and stored in 50% glycerol. The recombinant microorganism was designated as *E. coli* BL21 (DE3)/CJ_TH_F4E, and deposited at the Korean Culture Center of Microorganisms (KCCM) which is an international depositary authority under the provisions of the Budapest Treaty on Mar. 23, 2018 with Accession No. KCCM12235P.

Example 4-2: Production and Purification of Recombinant Enzyme

To prepare a recombinant enzyme CJ_TH_F4E from the recombinant microorganism *E. coli* BL21(DE3)/CJ_TH_F4E produced in Example 4-1, the recombinant microorganism was seeded in a culture tube containing 5 mL of an LB liquid medium with ampicillin antibiotic, and then seed culture was performed in a shaking incubator at 37° C. until absorbance at 600 nm reached 2.0. The culture obtained by the seed culture was seeded in a culture flask containing a liquid medium containing LB and lactose which is a protein expression regulator, and then main culture was performed. The seed culture and the main culture were performed under conditions of 180 rpm and 37° C. Then, the culture was centrifuged at 8,000 rpm and 4° C. for 20 minutes to recover cells. The recovered cells were washed with 50 mM Tris-HCl (pH 8.0) buffer twice and suspended in 50 mM NaH$_1$PO$_4$ (pH 8.0) buffer containing 10 mM imidazole and 300 mM NaCl. The suspended cells were disrupted using a sonicator. A cell lysate was centrifuged at 13,000 rpm and 4° C. for 20 minutes to take only a supernatant. The supernatant was purified by His-tag affinity chromatography, and 10 column volumes of 50 mM NaH$_2$PO$_4$ (pH 8.0) buffer containing 20 mM imidazole and 300 mM NaCl was applied to remove non-specifically bound proteins. Next, 50 mM NaH$_1$PO$_4$ (pH 8.0) buffer containing 250 mM imidazole and 300 mM NaCl was further applied to perform elution. Dialysis was performed using 50 mM Tris-HCl (pH 8.0) buffer to obtain CJ_TH_F4E which is a purified enzyme for enzyme characterization.

Example 4-3: Evaluation of Activity of Recombinant Enzyme to Convert Fructose into Tagatose To measure activity of CJ_TH_F4E which is the recombinant enzyme obtained in Example 4-2, 50 mM Tris-HCl (pH 8.0), 1 mM MnSO$_4$, and 4 mg/mL of CJ_TH_F4E were added to 1% by weight of fructose, and allowed to react at 55° C. for 4 hours.

Figure 11:
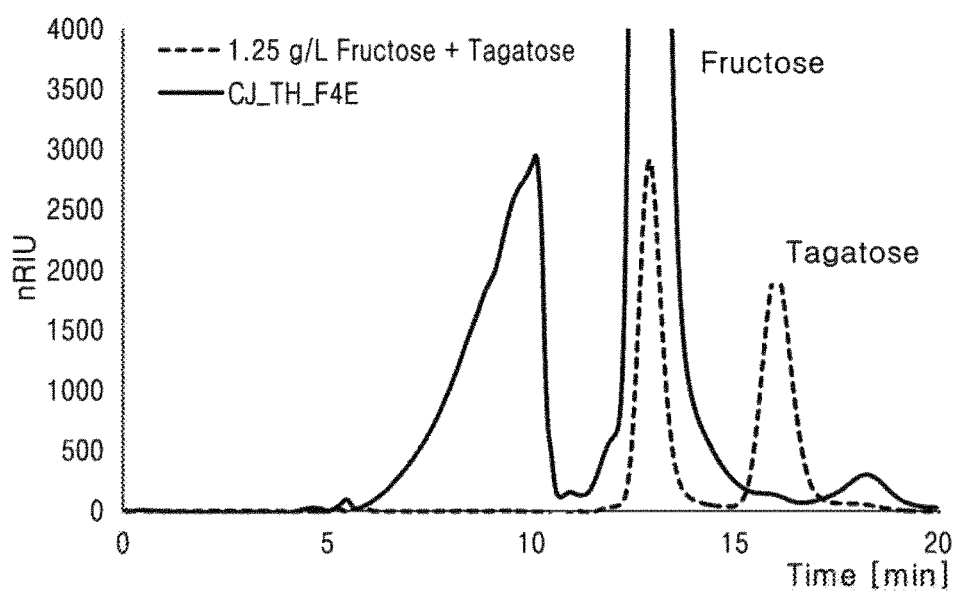
FIG. 11 is a result of HPLC chromatography showing that tagatose-6-phosphate kinase (CJ_TH_F4E) prepared in one embodiment of the present disclosure has fructose-4-epimerase activity.

Fructose remaining after reaction and a product tagatose were quantified by HPLC. HPLC was performed by using Shodex Sugar SP0810 as a column, and a temperature of the column was 80° C., and water as a mobile phase was applied at a flow rate of 1 mL/min (FIG. 11).

As a result, it was confirmed that the conversion rate from fructose into tagatose by the recombinant enzyme CJ_TH_F4E was 0.1%.

Example 5: Production of Tagatose-6-Phosphate Kinase and Evaluation of its Activity Example 5-1: Production of Recombinant Vector and Recombinant Microorganism Including Tagatose-6-Phosphate Kinase Gene To identify a novel heat-resistant fructose-4-epimerase, information of a tagatose-6-phosphate kinase gene derived from *Thermoanaerobacter indiensis* was obtained to prepare a recombinant vector expressible in *E. coli* and a transformed recombinant microorganism.

In detail, a nucleotide sequence of tagatose-6-phosphate kinase was selected from a nucleotide sequence of *Thermoanaerobacter indiensis*, which is registered in KEGG (Kyoto Encyclopedia of Genes and Genomes), and based on an amino acid sequence (SEQ ID NO: 11) and a nucleotide sequences (SEQ ID NO: 12) of the tagatose-6-phosphate kinase CJ_TAI_F4E derived from *Thermoanaerobacter indiensis*, pBT7-C-His-CJ_TAI_F4E which is a recombinant expression vector containing the nucleotide sequence of the enzyme and expressible in *E. coli* was synthesized (Bioneer Corp., Korea).

The recombinant vector was transformed into *E. coli* BL21(DE3) by heat shock transformation (Sambrook and Russell: Molecular cloning, 2001) to prepare a recombinant microorganism, and frozen and stored in 50% glycerol. The recombinant microorganism was designated as *E. coli* BL21 (DE3)/CJ_TAI_F4E, and deposited at the Korean Culture Center of Microorganisms (KCCM) which is an international depositary authority under the provisions of the Budapest Treaty on Mar. 23, 2018 with Accession No. KCCM12236P.

Example 5-2: Production and Purification of Recombinant Enzyme

To prepare a recombinant enzyme CJ_TAI_F4E from the recombinant microorganism *E. coli* BL21(DE3)/CJ_TAI_F4E produced in Example 5-1, the recombinant microorganism was seeded in a culture tube containing 5 mL of an LB liquid medium with ampicillin antibiotic, and then seed culture was performed in a shaking incubator at 37° C. until absorbance at 600 nm reached 2.0. The culture obtained by the seed culture was seeded in a culture flask containing a liquid medium containing LB and lactose which is a protein expression regulator, and then main culture was performed. The seed culture and the main culture were performed under conditions of 180 rpm and 37° C. Then, the culture was centrifuged at 8,000 rpm and 4° C. for 20 minutes to recover cells. The recovered cells were washed with 50 mM Tris-HCl (pH 8.0) buffer twice and suspended in 50 mM NaH$_2$PO$_4$ (pH 8.0) buffer containing 10 mM imidazole and 300 mM NaCl. The suspended cells were disrupted using a sonicator. A cell lysate was centrifuged at 13,000 rpm and 4° C. for 20 minutes to take only a supernatant. The supernatant was purified by His-tag affinity chromatography, and 10 column volumes of 50 mM NaH$_2$PO$_4$ (pH 8.0) buffer containing 20 mM imidazole and 300 mM NaCl was applied to remove non-specifically bound proteins. Next, 50 mM NaH$_2$PO$_4$ (pH 8.0) buffer containing 250 mM imidazole and 300 mM NaCl was further applied to perform elution. Dialysis was performed using 50 mM Tris-HCl (pH 8.0) buffer to obtain CJ_TAI_F4E which is a purified enzyme for enzyme characterization.

Example 5-3: Evaluation of Activity of Recombinant Enzyme to Convert Fructose into Tagatose To measure activity of CJ_TAI_F4E which is the recombinant enzyme obtained in Example 5-2, 50 mM Tris-HCl (pH 8.0), 1 mM MnSO$_4$, and 5 mg/mL of CJ_TAI_F4E were added to 5f by weight of fructose, and allowed to react at 55° C. for 10 hours.

Figure 12:
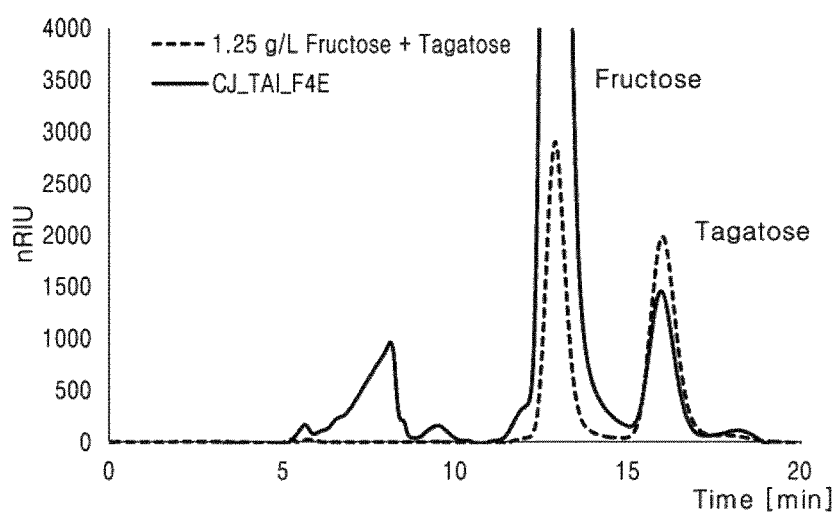
FIG. 12 is a result of HPLC chromatography showing that tagatose-6-phosphate kinase (CJ_TAI_F4E) prepared in one embodiment of the present disclosure has fructose-4-epimerase activity.

Fructose remaining after reaction and a product tagatose were quantified by HPLC. HPLC was performed by using Shodex Sugar SP0810 as a column, and a temperature of the column was 80° C., and water as a mobile phase was applied at a flow rate of 1 mL/min (FIG. 12).

As a result, it was confirmed that the conversion rate from fructose into tagatose by the recombinant enzyme CJ_TAI_F4E was 8.7%.

Effect of the Invention

Fructose-4-epimerase of the present disclosure has excellent heat resistance, produces tagatose at an industrial scale, and converts fructose as a common sugar into tagatose with a high yield, and thus is economically feasible.

International Depositary Authority: Korean Culture Center of Microorganisms (foreign)
Accession No.: KCCM11996P
Date of deposit: 20170320
International Depositary Authority: Korean Culture Center of Microorganisms (foreign)
Accession No: KCCM12093P
Date of deposit: 20170811
International Depositazy Authority: Korean Culture Center of Microorganisms (foreign)
Accession No: KCCM12109P
Date of deposit: 20170913
International Depositary Authority: Korean Culture Center of Microorganisms (foreign)
Accession No: KCCM12232P
Date of deposit: 20180323

International Depositary Authority: Korean Culture Center of Microorganisms (foreign)
Accession No: KCCM12235P
Date of deposit: 20180323

International Depositary Authority: Korean Culture Center of Microorganisms (foreign)
Accession No: KCCM12236P
Date of deposit: 20180323

What is claimed is:

1. A method of producing tagatose, the method consisting of:
   contacting fructose with an isolated enzyme consisting of the amino acid sequence of SEQ ID NO: 3 or 5 to convert the fructose into tagatose,
   and separating or purifying the tagatose.

2. The method of producing tagatose of claim 1, wherein the isolated enzyme is of the genus of *Dictyoglomus*.

3. The method of producing tagatose of claim 1, wherein the contacting is performed under conditions of pH 5.0 to pH 9.0 and 30° C. to 80° C. for 0.5 hours to 48 hours.

4. A method of producing tagatose, the method consisting of:
   contacting fructose with an isolated enzyme consisting of the amino acid sequence selected from the group consisting of SEQ ID NOs: 7, 9, and 11 to convert the fructose into tagatose,
   and separating or purifying the tagatose.

5. The method of producing tagatose of claim 4, wherein the isolated enzyme is of the genus of *Thermobifida* or of the genus of *Thermoanaerobacter*.

* * * * *